United States Patent
Falach et al.

(10) Patent No.: US 10,947,580 B2
(45) Date of Patent: Mar. 16, 2021

(54) DETECTION OF EXPOSURE TO RIP II TOXINS

(71) Applicant: The Israel Institute of Biological Research (IIBR), Ness-Ziona (IL)

(72) Inventors: Reut Falach, Tirat-Yehuda (IL); Ofir Israeli, Hod-Hasharon (IL); Ohad Shifman, Rehovot (IL); Adi Beth-Din, Mazkeret-Batia (IL); Tamar Sabo, Tel-Aviv (IL); Chanoch Kronman, Rehovot (IL)

(73) Assignee: THE ISRAEL INSTITUTE OF BIOLOGICAL RESEARCH (IIBR), Ness-Ziona (IL)

( * ) Notice: Subject to any disclaimer, the term of this patent is extended or adjusted under 35 U.S.C. 154(b) by 234 days.

(21) Appl. No.: 15/974,834

(22) Filed: May 9, 2018

(65) Prior Publication Data

US 2018/0327816 A1 Nov. 15, 2018

(30) Foreign Application Priority Data

May 9, 2017 (IL) .......................................... 252188

(51) Int. Cl.
  *C12Q 1/6809* (2018.01)
  *C12Q 1/686* (2018.01)
  *C12Q 1/6883* (2018.01)
  *C07K 14/42* (2006.01)
  *C12Q 1/6806* (2018.01)

(52) U.S. Cl.
  CPC ............ *C12Q 1/6809* (2013.01); *C07K 14/42* (2013.01); *C12Q 1/686* (2013.01); *C12Q 1/6883* (2013.01); *C12Q 1/6806* (2013.01)

(58) Field of Classification Search
  None
  See application file for complete search history.

(56) References Cited

U.S. PATENT DOCUMENTS

2016/0060698 A1* 3/2016 Tomizawa ........... C12Q 1/6883
  435/6.11
2018/0171385 A1* 6/2018 Lowe ................... C12Q 1/6806

OTHER PUBLICATIONS

Chung, Application of deadenylase electrochemiluminescence assay for ricin to foods in a plate format, Journal of Food Protection, 72(4):903-906 (2009).
Bozza, et al., Ricin detection: Tracking active toxin, Biotechnology Advances, 2015, pp. 117-123, vol. 33.
Chiou, et al., The ribosomal stalk is required for ribosome binding, depurination of the rRNA and cytotoxicity of ricin A chain in *Saccharomyces cerevisiae*, Mol. Microbiol., Dec. 2008, pp. 1441-1452, vol. 70(6).
Falach, et al., Quantitative profiling of the in vivo enzymatic activity of recin reveals disparate depurination of different pulmonary cell types, Toxicology Letters, 2016, pp. 11-19, vol. 258.

(Continued)

*Primary Examiner* — Samuel C Woolwine
(74) *Attorney, Agent, or Firm* — Browdy and Neimark, PLLC

(57) ABSTRACT

The invention concerns methods for detecting exposure to a RIP II family toxin in a biological sample. The method is based on identifying the enzymatic activity of the toxin on 28sRNA and employs sensitive and specific amplification steps that allow detection in clinical samples.

18 Claims, 7 Drawing Sheets

Specification includes a Sequence Listing.

(56) References Cited

OTHER PUBLICATIONS

Falach, et al., Identifying exposures to ribosome-inactivating proteins in blood samples: amplification of ricin-induced ribosomal damage products enables sensitive detection of active toxin and circulating depurinated 28S rRNA, Forensic Toxicology, 2018, pp. 1-10.
Gaylord, et al., Ultrasensitive Detection of Ricin Toxin in Multiple Sample Matrixes Using Single-Domain Antibodies, Anal. Chem., 2015, pp. 6570-6577, vol. 87.
He, et al., Ricin Toxicokinetics and Its Sensitive Detection in Mouse Sera or Feces Using Immuno-PCR, PLos ONE, Sep. 2010, pp. 1-8, vol. 5, issue 9.
Iordanov, et al., Molecular and Cellular Biology, Jun. 1997, pp. 3373-3381, vol. 17, No. 6.
Israeli, et al., Determination of ricin intoxication in biological samples by monitoring depurinated 28S rRNA in a unique reverse transcription-ligase-polymerase chain reaction assay, Forensic Toxicol., 2018, pp. 72-80, vol. 36.
Lubelli, et al., Detection of ricin and other ribosome-inactivating proteins by an immuno-polymerase chain reaction assay, Analytical Biochemistry, 2006, pp. 102-109, vol. 355.
Melchior, et al., A functional quantitative polymerase chain reaction assay for ricin, Shiga toxin, and related ribosome-inactivating proteins, Analytical Biochemistry, 2010, pp. 204-211, vol. 396.
Musshoff, et al., Ricin poisoning and forensic toxicology, Drug Test. Analysis, 2009, pp. 184-191, vol. 1.
Pierce, et al., Development of a quantitative RT-PCR assay to examine the kinetics of ribosome depurination by ribosome inactivating proteins using *Saccharomyces cerevisiae* as a model, RNA, 2011, pp. 201-210, vol. 17.
Puri, et al., Integrating Immunobased Detection and Identification Methods for Ricin Analysis: An Overview, J. Bioterr Biodef, 2011, pp. 1-7.
Schrot, et al., Ribosome-Inactivating and Related Proteins, Toxins, 2015, pp. 1556-1615, vol. 7.
Tanpure, et al., Label-free fluorescence detection of the depurination activity of ribosome inactivating protein toxins, Chem. Commun., 2012, pp. 501-503, vol. 48.
Wu, et al., Immunochromatography Detection of Ricin in Environmental and Biological Samples, 2011, pp. 169-173, vol. 3(3).
Yan, et al., N-glycosylation does not affect the catalytic activity of ricin A chain but stimulates cytotoxicity by promoting is transport out of the endoplasmic reticulum, Traffic, Nov. 2012, pp. 1508-1521, vol. 13(11).
Zhao, et al., Detection of Ricin Intoxication in Mice Using Serum Peptide Profiling by MALDI-TOF/MS, International Journal of Molecular Sciences, 2012, pp. 13704-13712, vol. 13.
Zhao, et al., Rapid Detection of Ricin in Serum Based on Cu-Chelated Magnetic Beads Using Mass Spectrometry, J. Am. Soc. Mass. Spectrom., 2016, pp. 748-751, vol. 27.

\* cited by examiner

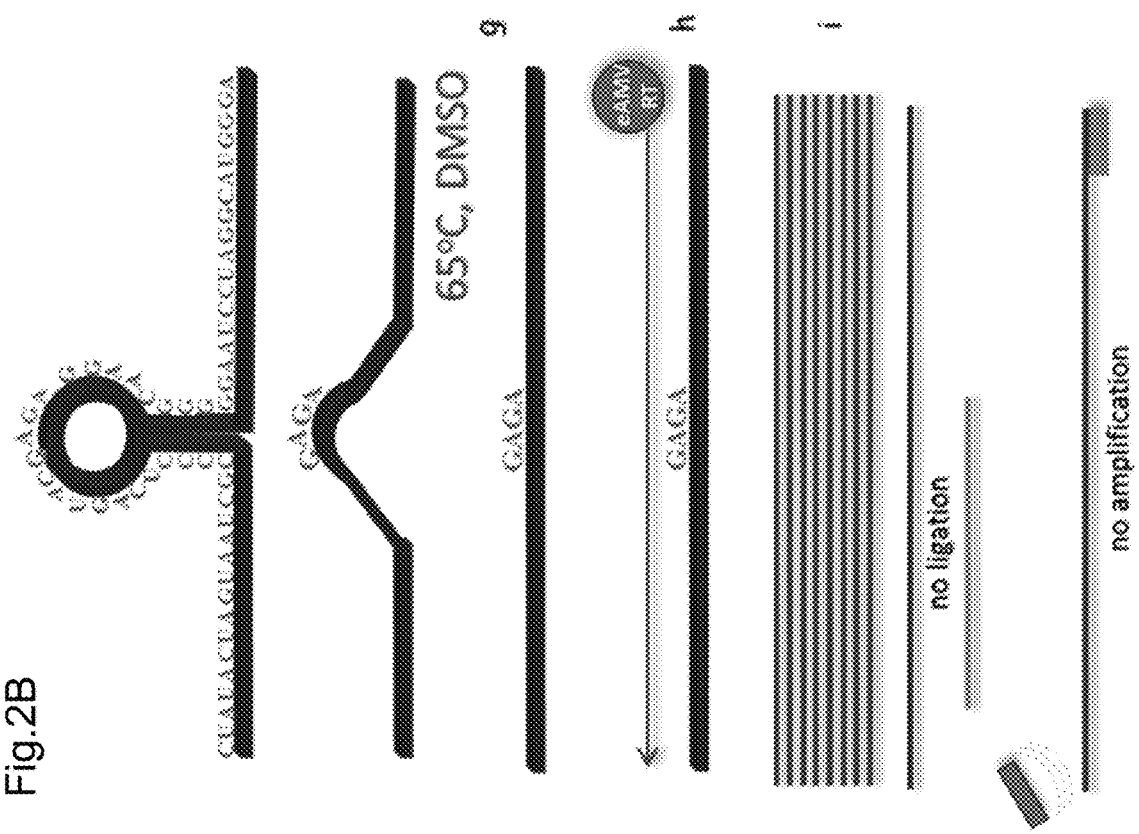
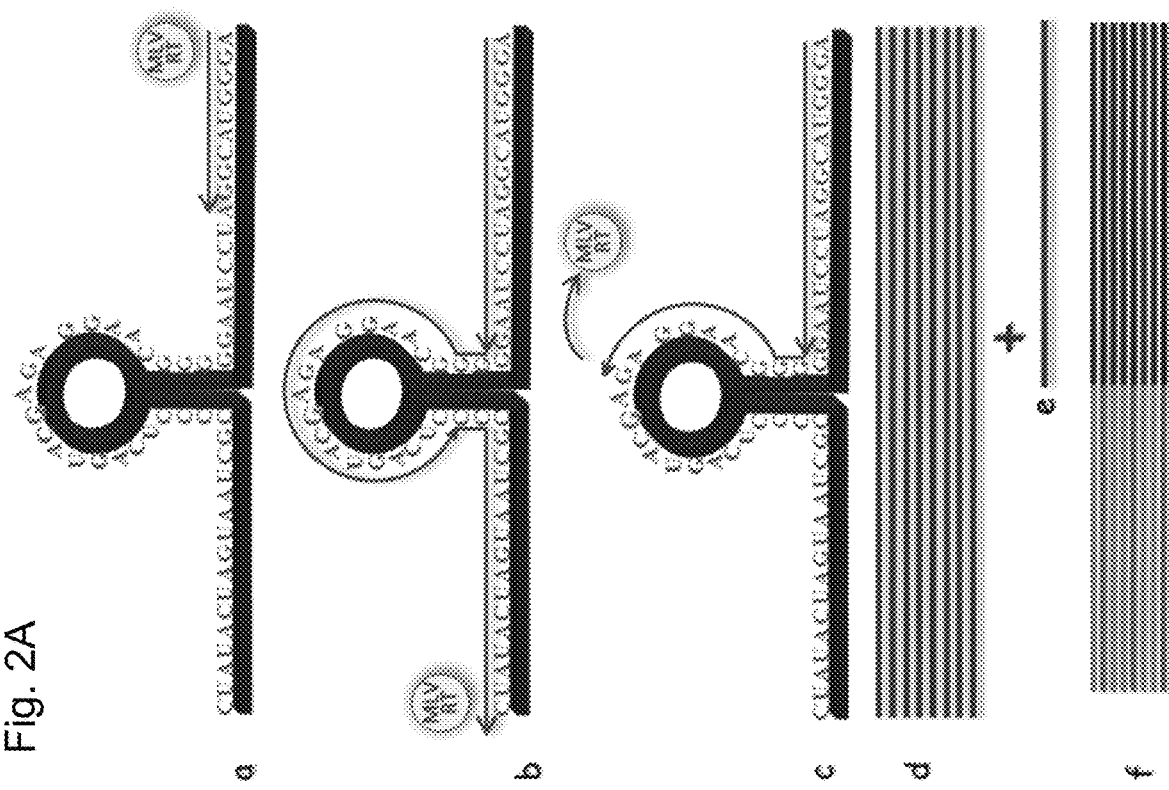
Fig. 2A
Fig. 2B

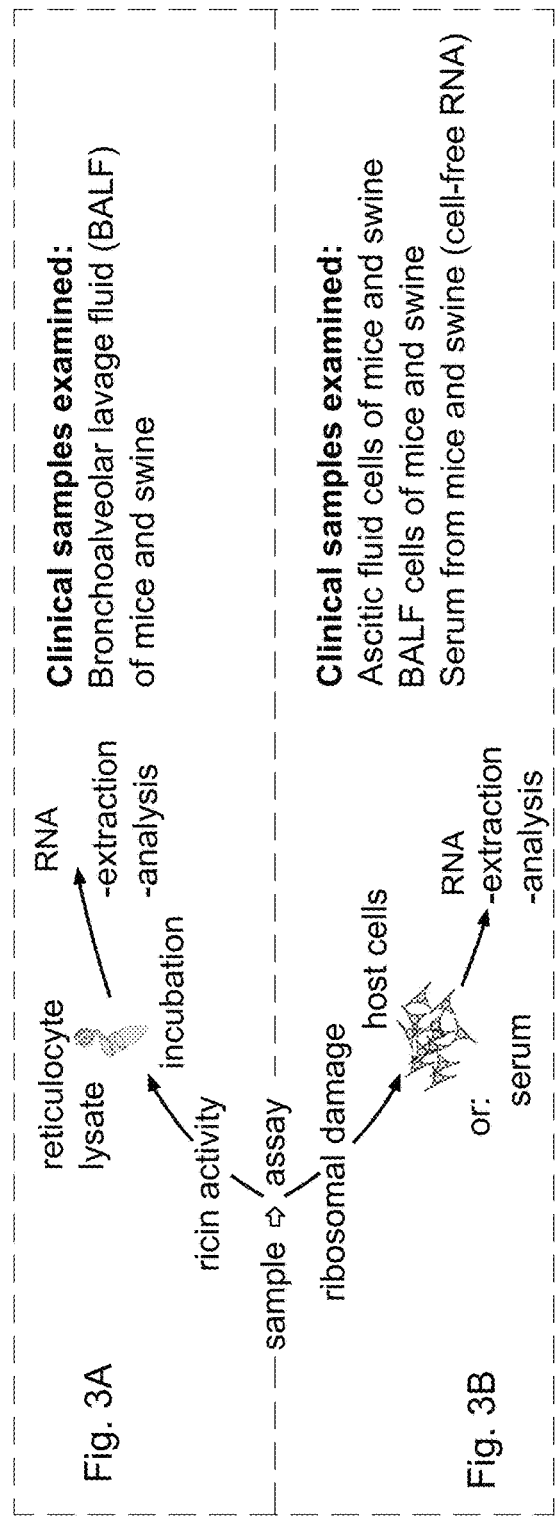
Fig. 3A
Fig. 3B
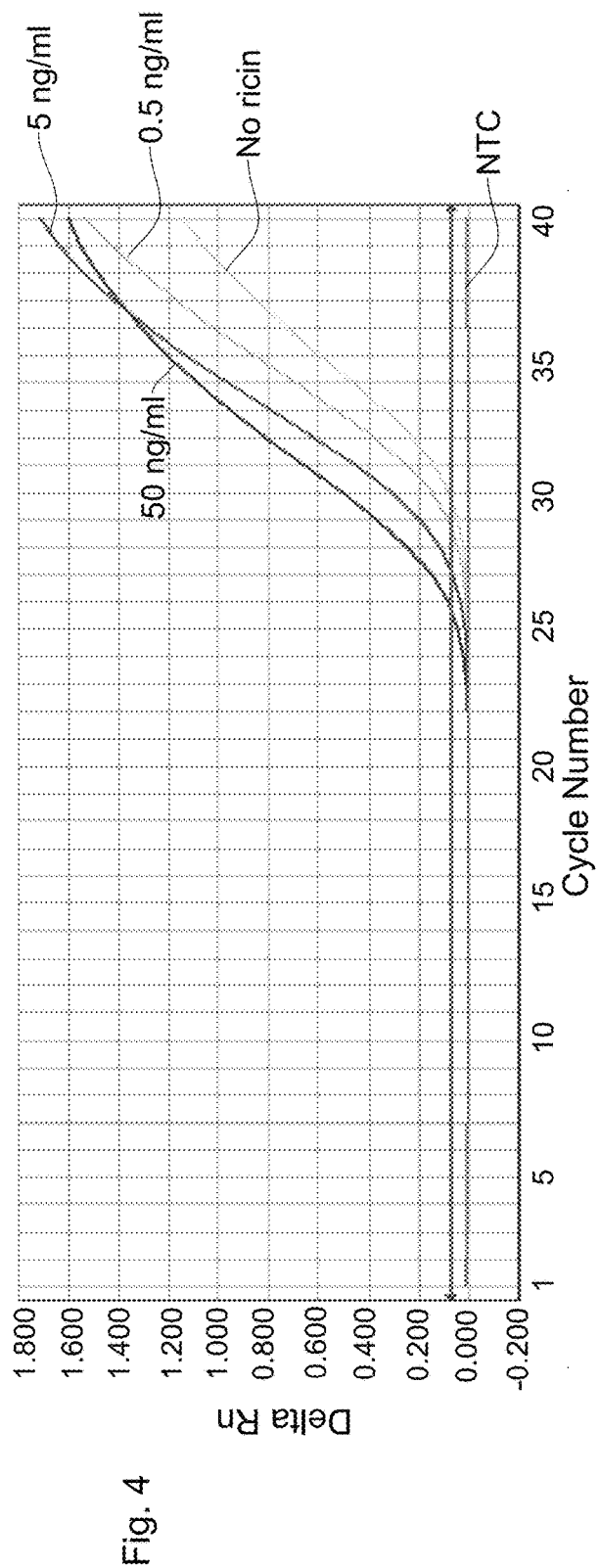
Fig. 4

DETECTION OF EXPOSURE TO RIP II TOXINS

The Sequence Listing in ASCII text file format of 2,409 bytes in size, created on Jul. 30, 2020, with the file name "2020-08-03SeqListing-FALACH1," filed in the U.S. Patent and Trademark Office on even date herewith, is hereby incorporated herein by reference.

TECHNOLOGICAL FIELD

The present invention relates to the detection of intoxication with a RIP II toxin, in particular ricin intoxication of human subjects.

BACKGROUND ART

References considered to be relevant as background to the presently disclosed subject matter are listed below:
1. Schrot J. et al, *Toxins* (Basel). 2015; 7(5):1556-615.
2. Iordanov M S. et al, *Mol Cell Biol.* 1997; 17(6):3373-81.
3. Chiou J C. et al, *Mol Microbiol.* 2008; 70(6):1441-52.
4. Falach R. et al, *Toxicol Lett.* 2016 Sep. 6; 258:11-9.
5. Melchior W B. Jr. and Tolleson W H., *Anal Biochem.* 2010; 396(2):204-11.
6. Pierce M. et al, *RNA.* 2011; 17(1):201-10.
7. Yan Q. et al, *Traffic.* 2012; 13(11):1508-21.
8. Tanpure A A. et al, *Chem. Commun* 2012; 48:501-503.
9. Bozza W P. et al, *Biotechnol Adv.* 2015; 33(1):117-23.

Acknowledgement of the above references herein is not to be inferred as meaning that these are in any way relevant to the patentability of the presently disclosed subject matter.

BACKGROUND

Ribosome-inactivating proteins (RIPs) are toxins that act as RNA-N-glycosidases. These toxins are classified as type I RIPS and type II RIPs. The type II RIP family of toxins includes several members such as the plant toxins ricin and abrin and the bacterial Shiga toxin. The RNA-N-glycosidase activity of the RIP toxins causes depurination of a specific nucleotide in the 28S-rRNA at the position corresponding to $A_{4324}$ in rats (1).

Based on its ability to catalyze sequence specific RNA damage in the 28S-rRNA, Iordanov et al (2) developed an experimental assay to monitor the in vivo ricin A chain-induced depurination of $A_{4324}$ based on lesion-induced arrest of a reverse transcriptase-driven primer extension. The reaction products were subsequently electrophoresed on sequencing gels and their sequence was determined.

This method was further used in other studies aimed at the understanding of the mechanism of action of the ricin toxin, e.g. by Chiou et al (3).

Falach et al (4) employed the reverse transcriptase-driven primer extension assay to quantify the depurination process that occurs in vivo in the lungs of mice exposed to the ricin toxin. The authors monitored truncated cDNA molecules which are formed by reverse transcription when a depurinated 28S rRNA serves as template. The amount of the truncated molecules was determined by capillary electrophoresis fragment analysis of the reaction products.

Melchior and Tolleson (5) used a functional polymerase chain reaction (PCR) assay to quantify ricin, Shiga toxin and other related ribosome-inactivating proteins. The authors used a reverse transcriptase (RT) enzyme which preferentially inserts an adenine opposite to an abasic site in RNA. Use of this RT enzyme in the assay results in the generation of a cDNA strand that is different by one nucleotide from a cDNA generated on the basis of a non-damaged 28S rRNA. This difference serves to distinguish between a normal and a depurinated 28S rRNA. The authors used this assay to study enzymatic properties of ricin.

This method was used in other studies to characterize ricin kinetics in yeast (6), or to study ricin's catalytic activity (7).

A method of label-free fluorescence detection of the depurination activity of ribosome inactivating protein toxins was described in Tanpure A A. et al (8), however detection of depurination according to this method, involves the use of a synthetic RNA molecule as substrate, is feasible only at high concentrations of toxin within the micromolar range and is not suitable for detection in clinical samples.

A review article by Bozza et al (9) summarizes the known methods for detection of ricin.

Despite the existence of several such methods, none of the known methods is suitable for identifying minute amounts of the toxin (pg/ml), as required for detecting RIP II poisoning in clinical samples.

GENERAL DESCRIPTION

In a first of its aspects, the present invention provides a method for detecting exposure to a RIP II family toxin in a biological sample, the method comprising the steps of:
  a. Obtaining an isolated RNA preparation comprising 28S rRNA;
  b. Performing a reverse transcriptase (RT) reaction using a primer complementary to a sequence of the 28S rRNA which is positioned 3' to the RIP II family enzyme depurination site, whereby a truncated cDNA transcript is formed if the 28S rRNA was exposed to a RIP II family toxin and was depurinated;
  c. Labeling said truncated cDNA transcript obtained in step (b) by ligating a synthetic nucleic acid (e.g. DNA) strand at the truncated 3' end of the transcript, thereby obtaining a chimeric ligation product; and
  d. Amplifying the chimeric ligation product using polymerase chain reaction (PCR);
wherein detection of an amplified chimeric ligation product indicates exposure to a RIP II family toxin.

In one embodiment, prior to step (a) said isolated RNA preparation comprising 28S rRNA is incubated with a biological sample obtained from a subject suspected of exposure to a RIP II family toxin.

Therefore, according to this embodiment, the present invention provides a method for detecting a RIP II family toxin in a biological sample, the method comprising the steps of:
  a. Incubating said biological sample with a composition comprising 28S rRNA;
  b. Isolating RNA from said composition comprising 28S rRNA;
  c. Performing a reverse transcriptase (RT) reaction using a primer complementary to a sequence of the 28S rRNA which is positioned 3' to the RIP II family enzyme depurination site, whereby a truncated cDNA transcript is formed if the 28S rRNA was exposed to a RIP II family toxin and was depurinated;
  d. Labeling said truncated cDNA transcript obtained in step (c) by ligating a synthetic nucleic acid (e.g. DNA) strand at the truncated 3' end of the transcript, thereby obtaining a chimeric ligation product; and
  e. Amplifying the chimeric ligation product using polymerase chain reaction (PCR);

wherein detection of an amplified chimeric ligation product indicates that said biological sample contains RIP II family toxins.

In another embodiment, said isolated RNA preparation comprising 28S rRNA of step (a) is isolated from a biological sample obtained from a subject suspected of exposure to a RIP II family toxin.

Therefore, according to this embodiment, the present invention provides a method for detecting ribosomal damage induced by exposure to RIP II family toxins in a biological sample, the method comprising the steps of:

a. Isolating RNA from a biological sample, wherein the isolated RNA comprises 28S rRNA;

b. Performing a reverse transcriptase (RT) reaction using a primer complementary to a sequence of the 28S rRNA which is positioned 3' to the RIP II family enzyme depurination site, whereby a truncated cDNA transcript is formed if the 28S rRNA was exposed to a RIP II family toxin and was depurinated;

c. Labeling said truncated cDNA transcript obtained in step (b) by ligating a synthetic nucleic acid strand at the truncated 3' end of the transcript, thereby obtaining a chimeric ligation product; and d. Amplifying the chimeric ligation product using PCR;

wherein detection of an amplified chimeric ligation product indicates the presence of ribosomal damage induced by exposure to RIP II family toxins in said biological sample.

In one embodiment, the method further comprises a step of opening the rRNA secondary structure in said isolated RNA during said reverse transcriptase step.

In one embodiment, said step of opening the rRNA secondary structure is performed by adding DMSO to the reaction.

In one embodiment, the reverse transcriptase (RT) reaction is performed at an elevated temperature.

In one specific embodiment, the elevated temperature is between about 50° C. and 75° C., e.g. about 65° C.

In one embodiment, a thermostable reverse transcriptase enzyme is used in the reaction.

In one embodiment, the thermostable reverse transcriptase enzyme is RT-eAMV enzyme.

In one embodiment, said biological sample is a clinical sample.

In one embodiment, said biological sample is selected from the group consisting of blood, serum, bronchoalveolar lavage fluid, ascitic fluid, nasal lavage fluid, scraping of nose cells, palate, cheek, urine and semen.

In one embodiment, the RIP II family toxins are selected from the group consisting of ricin, abrin, shiga, alpha sarcin, saporin, modeccin, volkensin and Mistletoe lectin I.

In one embodiment, the RIP II family toxin is ricin.

In one embodiment, said ligation of a synthetic DNA strand to the truncated cDNA transcript is performed by adding to the ligation reaction a DNA probe having a sequence capable of hybridizing with the 3' terminus of said truncated cDNA transcript and a consecutive sequence capable of hybridizing with the 5' terminus of said synthetic DNA strand.

In one embodiment, the PCR is quantitative real time PCR.

In one embodiment, the present invention provides a method of detection of exposure to a RIP II family toxin in a biological sample, comprising performing both the method for detecting a RIP II family toxin as described above and the method for detecting ribosomal damage induced by exposure to RIP II family toxins, as described above.

In one embodiment, the biological sample is obtained from 1 hour to 120 hours post exposure to the RIP II family toxin.

In another aspect, the present invention provides a kit comprising:

(a) a synthetic DNA strand;

(b) a DNA dual oligonucleotide having a sequence capable of hybridizing with the 3' terminus of a truncated cDNA transcript of a portion of the 28S rRNA obtained by an RT reaction upon depurination by a RIP II family toxin and a consecutive sequence capable of hybridizing with the 5' terminus of said DNA synthetic strand;

(c) DNA primers having a sequence capable of hybridizing with the 3' terminus of the synthetic DNA strand;

(d) DNA primers having a sequence capable of hybridizing with the 5' terminus of said truncated cDNA transcript (e) a container; and optionally (f) instructions for use in detecting exposure to a RIP II family toxin in a biological sample.

In one embodiment, the kit further comprises:

(g) a DNA primer having a sequence capable of hybridizing with a sequence of the 28S rRNA which is positioned upstream to the RIP II family enzyme depurination site; and optionally (h) a reverse transcriptase enzyme; and optionally (i) a ligase enzyme; and optionally (j) DNA polymerase enzyme; and optionally (k) buffers for performing each of the reactions; and optionally (l) dNTPs.

In one embodiment, the kit further comprises an agent for opening the rRNA secondary structure.

In one embodiment, said agent for opening the rRNA secondary structure is DMSO.

In one embodiment, the reverse transcriptase is active at an elevated temperature.

In one embodiment, said elevated temperature is between about 50° C. and 75° C., e.g. about 65° C.

In one embodiment, the reverse transcriptase enzyme is RT-eAMV enzyme.

In one embodiment, the kit further comprises a DNA target probe with a fluorescent reporter at the 5' end and a quencher of fluorescence at the 3' end having a sequence capable of hybridizing with said DNA dual probe.

In one embodiment, said biological sample is a clinical sample.

In one embodiment, the clinical sample is selected from the group consisting of blood, serum, bronchoalveolar lavage fluid, ascitic fluid, nasal lavage fluid, scraping of nose cells, palate or cheek, urine and semen.

In one embodiment, the biological sample is obtained from 1 hour to 120 hours post exposure to the RIP II family toxin.

In one embodiment, said RIP II family toxin is selected from the group consisting of ricin, abrin, shiga, alpha sarcin, saporin, modeccin, volkensin and Mistletoe lectin I.

In one embodiment, the RIP II family toxin is ricin.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 2A-2B—Schematic comparison of the assay conditions of the method of the invention performed without prior melting of the secondary structure of the 28SrRNA (A) and with prior melting of the secondary structure of the 28SrRNA (B). The sequence of the 28S rRNA ricin target-site region is depicted in SEQ ID NO:9.

FIGS. 3A-3B—Schematic representation of the two modes of the method of the invention for highly-sensitive detection of exposure to ricin in clinical samples. FIG. 3A is a schematic representation for detection of ricin activity. FIG. 3B is a schematic representation for detection of ribosomal damage.

FIG. 4—Detection of ricin-induced 28S rRNA truncated cDNA copies following incubation of reticulocyte lysates with different amounts of ricin. Graph showing Delta Rn versus Cycle number when Rn is the reporter signal normalized to the signal of the ROX dye; Delta Rn is Rn minus the baseline; NTC means no template control. The different curves indicate different final concentrations of ricin added to the reticulocyte lysates (0.5-50 ng/ml). Analysis was performed using Auto baseline and Auto Ct (cycle threshold).

FIG. 5—Detection of ricin-induced 28S rRNA truncated cDNA copies (after melting the secondary structure of 28S rRNA) following incubation of reticulocyte lysates with different amounts of ricin. Graph showing Delta Rn versus Cycle number when Rn is the reporter signal normalized to the signal of the ROX dye; Delta Rn is Rn minus the baseline; NTC means no template control. The different curves indicate different final concentrations of ricin into reticulocyte lysates 0.005-50 ng/ml. Analysis was performed using Auto baseline and Auto Ct (cycle threshold).

FIG. 6—Detection of enzymatically-active ricin in broncheoalveolar fluid (BALF) harvested from mice 72 hours after intranasal exposure to ricin. Graph showing Delta Rn versus Cycle number when Rn is the reporter signal normalized to the signal of the ROX dye; Delta Rn is Rn minus the baseline; NTC means no template control. The different curves indicate different mice. Analysis was performed using Auto baseline and Auto Ct (cycle threshold).

FIG. 7—Detection of enzymatically-active ricin in broncheoalveolar fluid (BALF) harvested from swine 30 hours after intratracheal exposure to ricin. Graph showing Delta Rn versus Cycle number when Rn is the reporter signal normalized to the signal of the ROX dye; Delta Rn is Rn minus the baseline; NTC means no template control. The different curves indicate different swine. Analysis was performed using Auto baseline and Auto Ct (cycle threshold).

FIG. 8—Detection of ricin-induced ribosomal damage in cells harvested from BALF of swine 30 hours after intratracheal exposure to ricin. Graph showing Delta Rn versus Cycle number when Rn is the reporter signal normalized to the signal of the ROX dye; Delta Rn is Rn minus the baseline; NTC means no template control. The different curves indicate different swine. Analysis was performed using Auto baseline and Auto Ct (cycle threshold).

FIG. 9—Detection of ricin-induced ribosomal damage, in cells harvested from the ascitic fluid of mice 48 hours after intraperitoneal exposure to ricin. Graph showing Delta Rn versus Cycle number when Rn is the reporter signal normalized to the signal of the ROX dye; Delta Rn is Rn minus the baseline; NTC means no template control. The 48 hours curve results from analysis of the pooled ascitic fluid of 10 mice. Analysis was performed using Auto baseline and Auto Ct (cycle threshold).

FIG. 10—Detection of ricin-induced ribosomal damage, in cells harvested from ascitic fluid of swine 18 hours after intraperitoneal exposure to ricin. Graph showing Delta Rn versus Cycle number when Rn is the reporter signal normalized to the signal of the ROX dye; Delta Rn is Rn minus the baseline; NTC means no template control. The 18 hours curve is for one swine. Analysis was performed using Auto baseline and Auto Ct (cycle threshold).

FIG. 11—Detection of ricin-induced ribosomal damage in serum collected from intoxicated mice 48 hours after intraperitoneal exposure to ricin. Graph showing Delta Rn versus Cycle number when Rn is the reporter signal normalized to the signal of the ROX dye; Delta Rn is Rn minus the baseline; NTC means no template control. The 48 hours curve is an average curve resulting from analysis of 10 mice. Analysis was performed using Auto baseline and Auto Ct (cycle threshold).

FIG. 12—Detection of ricin-induced ribosomal damage in serum collected from an intoxicated swine 18 hours after intraperitoneal exposure to ricin. Graph showing Delta Rn versus Cycle number when Rn is the reporter signal normalized to the signal of the ROX dye; Delta Rn is Rn minus the baseline; NTC means no template control. The 18 hours curve is for one swine. Analysis was performed using Auto baseline and Auto Ct (cycle threshold).

DETAILED DESCRIPTION OF EMBODIMENTS

The present invention is based on the development of a uniquely sensitive assay that allows the detection of exposure to a RIP II family toxin in clinical samples.

The 28S rRNA serves as a substrate for RIP II family toxins. As a result of the toxins' activity the 28S rRNA is depurinated at a certain position. By subjecting the damaged ribosome to a reverse transcriptase reaction, a unique truncated cDNA molecule is formed as a result of the toxin's catalytic activity.

If the ribosome was exposed to a RIP II family toxin, the 28S rRNA template for the RT reaction contains a depurinated position. The activity of the RT enzyme is stopped because of the missing nucleotide at the depurinated position and a short (truncated) cDNA strand is formed.

Methods of the prior art identify the truncated cDNA strand thus obtained by sequencing of the reaction product. However, in order to identify ribosomal damage products in clinical samples which are usually of a relatively small volume, the sensitivity of the method must be largely enhanced.

The inventors of the present invention developed a unique method for enhancing the sensitivity of the detection method. The truncated cDNA products that are obtained by the reverse transcriptase-driven primer extension reaction are logarithmically enhanced using a PCR reaction with unique labels for the truncated cDNA sequences.

The method of the invention therefore combines reverse transcriptase-driven primer extension forming a unique, truncated cDNA molecule, ligation with a synthetic single strand DNA molecule (also termed herein "synthetic DNA strand"), and a PCR reaction which specifically amplifies only the cDNA sequence that was generated in ribosomes that were damaged by a RIP II toxin, and thereby indicates exposure to the toxin.

Figures 1A, 1B:
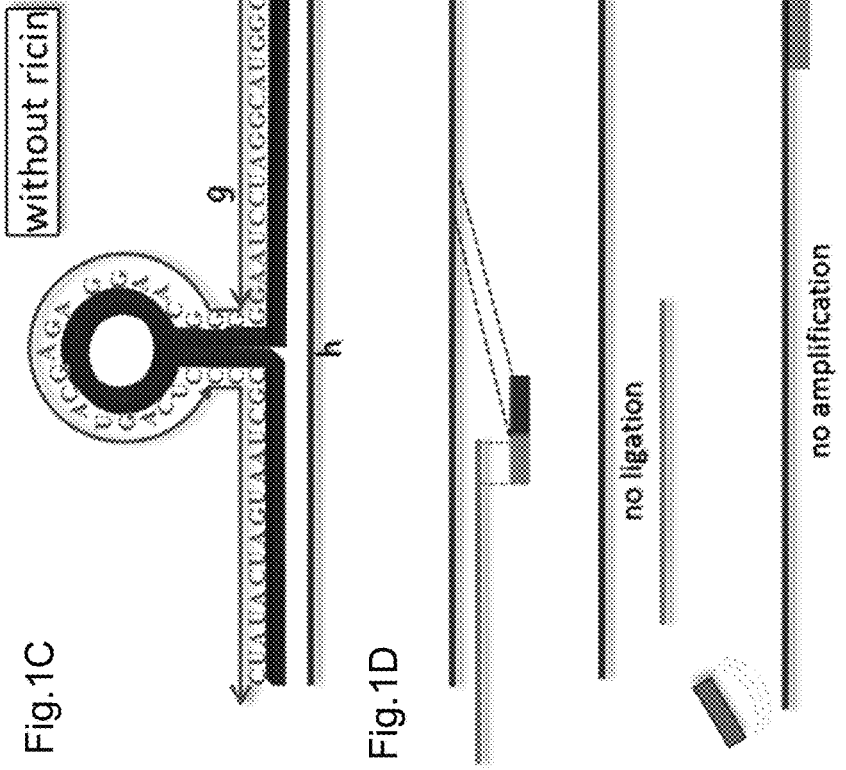
FIGS. 1A-1D—Schematic representations of the method of the invention for sensitive detection of exposure to ricin in clinical samples. The sequence of the 28S rRNA ricin target-site region after depurination by ricin is depicted in SEQ ID NO:8 (FIG. 1A). The sequence of the 28S rRNA ricin target-site region without exposure to ricin is depicted in SEQ ID NO:9 (FIG. 1C).

Generally, the detection method comprises the following steps:

a. Providing an RNA sample, wherein the RNA sample comprises 28S RNA.
b. Performing a reverse transcriptase (RT) reaction, whereby a cDNA transcript of a portion of the 28sRNA is formed.
c. The primer for the RT reaction is selected such that the generated transcript includes the putative RIP II family toxin depurination site, e.g. at position $A_{4324}$. If the 28S rRNA was depurinated as a result of RIP II poisoning, a truncated transcript is generated.
d. The truncated RT transcript (i.e. the cDNA molecule) is labeled by adding a unique, heterologous synthetic DNA strand at the truncated end (3' terminus). This is performed by incubating the cDNA molecule and the synthetic strand together with a complementary dual oligonucleotide (also termed herein "dual oligonucleotide") comprising a sequence that complements that of the 3' end of the cDNA molecule and the 5' end of the synthetic strand, and then annealing the cDNA molecule to the synthetic strand in a ligation reaction, thereby obtaining a unique chimeric molecule composed of the truncated cDNA strand and the synthetic strand.
e. Amplifying the chimeric molecule using quantitative real-time PCR.

Therefore, in a first of its aspects, the present invention provides a method for detecting exposure to a RIP II family toxin in a biological sample, the method comprising the steps of:

a. Obtaining an isolated RNA preparation comprising 28S rRNA;
b. Performing a reverse transcriptase (RT) reaction using a primer complementary to a sequence of the 28S rRNA which is positioned 3' to the RIP II family enzyme depurination site, whereby a truncated cDNA transcript is formed if the 28S rRNA was exposed to a RIP II family toxin and was depurinated;
c. Labeling said truncated cDNA transcript obtained in step (b) by ligating a synthetic nucleic acid (e.g. DNA) strand at the truncated 3' end of the transcript, thereby obtaining a chimeric ligation product; and
d. Amplifying the chimeric ligation product using polymerase chain reaction (PCR);
wherein detection of an amplified chimeric ligation product indicates exposure to a RIP II family toxin.

The method described in this invention can be applied in two different modes to identify exposure to a RIP II family toxin (e.g. ricin). In a first mode, clinical samples obtained from the subject are assayed directly for the presence of the toxin. This is achieved by incubating the sample with a composition comprising rRNA (e.g. a reticulocyte lysate), followed by extraction of the RNA and its analysis for the presence of the truncated cDNA product as described above. This mode of application allows one to determine the presence of an active toxin in the clinical sample.

In a second mode, clinical samples obtained from the subject are assayed for ribosomal damage as a measure of the toxin's activity. This is achieved by extraction of cellular RNA or of circulating cell-free RNA from the sample, and its analysis for the presence of the truncated cDNA product, as described above. This mode of application allows one to determine that ribosomes of the subject have been impaired by the action of ricin toxin.

In certain embodiments the clinical samples obtained from a subject can be tested using both modes thereby detecting the presence of a RIP II family toxin, or identifying its injurious activity by detecting toxin-induced ribosomal damage in the sample. Largely, the first mode which identifies the toxin itself, is expected to be most suitable at earlier time-points following exposure to toxin, while the second mode which detects ribosomal damage in the clinical sample is expected to be most suitable at later time-points following exposure to toxin.

In one embodiment, the limit of detection of the method which identifies the toxin itself is ~5 pg ricin/ml. In one embodiment, the limit of detection of the method which detects ribosomal damage is ~0.15 µg ricin/kg body weight.

Therefore, in one aspect which corresponds to the first mode described above, the present invention provides a method for detecting a RIP II family toxin in a biological sample, the method comprising the steps of:

a. Incubating said biological sample with a composition comprising 28S rRNA;
b. Isolating total RNA from said composition comprising 28S rRNA;
c. Performing a reverse transcriptase (RT) reaction using a primer complementary to a sequence of the 28S rRNA which is positioned 3' to the RIP II family enzyme depurination site, whereby a truncated cDNA transcript is formed if the rRNA was exposed to a RIP II family toxin and was depurinated;
d. Labeling said truncated cDNA transcript obtained in step (c) by ligating a synthetic nucleic acid (e.g. DNA) strand at the truncated 3' end of the transcript,
thereby obtaining a chimeric ligation product; and
e. Amplifying the chimeric ligation product using PCR;
wherein detection of an amplified chimeric ligation product indicates that said biological sample contains RIP II family toxins.

As used herein the term "detecting" refers to discovering or evidencing the presence of an element or an analyte or a target molecule in a biological/clinical sample. In the context of the present invention the term detecting refers to examining whether a toxin is or was present in a biological/clinical sample. In specific embodiments the term refers to the identification of a RIP II family toxin or to ribosomal damage induced by exposure to a RIP II family toxin.

As used herein the term "RIP family toxin" refers to a group of toxins known as Ribosome-inactivating proteins, which are mainly produced by plants and act as N-glycosidases (i.e. enzymes that hydrolyze glycosidic bonds), thereby inhibiting protein synthesis by cleaving a specific adenine residue from the large subunit of the ribosomal RNA. There are two major types of Ribosome-inactivating proteins: type 1 Ribosome-inactivating proteins (RIP I) and type 2 Ribosome-inactivating proteins (RIP II). Type 1 RIPs are single chain proteins, whereas type 2 RIPs consist of two polypeptide chains (A- and B-chain) that are usually linked through a disulfide bridge. The A-chain contains the enzymatic function and the B-chain has lectin properties enabling these proteins to bind to galactose residues on the cell surface. This facilitates the A-chain to enter the cell. Examples of RIP family proteins/toxins can be found in Schrot J. et al (1). Non-limiting examples of RIP II family toxins encompassed by the present invention are ricin, abrin, shiga, alpha sarcin, saporin, modeccin, volkensin and Mistletoe lectin I.

In a specific embodiment, the invention concerns an enzymatically-active RIP II family toxin. As used herein the term "enzyme" refers to a protein which allows the activation or the acceleration of a chemical reaction. The term "enzymatically-active" refers to the condition of an enzyme wherein such enzyme is able to perform its characteristic activity, e.g. an enzymatically active RIP II toxin performs a depurination reaction.

As used herein the term "depurination" refers to a chemical reaction of the purine nucleic acids, adenosine or guanosine, in which the β-N-glycosidic bond is hydrolytically cleaved releasing a nucleic base, adenine or guanine, respectively. Specifically, as used herein the term refers to a RIP enzyme activity in which a specific adenine residue is cleaved from the large subunit of the ribosomal RNA. This results in the formation of a-basic sites which in turn, causes the ribosome containing the a-basic site to have a lower affinity to elongation factors that are crucial for protein synthesis, ultimately leading to cell death.

The term "depurination site" refers to the specific site of cleavage by RIP of the aforementioned adenine residue. This depurination site, which corresponds to $A_{4324}$ in the rat liver 28S rRNA, is universally conserved in mammalians, humans included.

As used herein, the term "28S rRNA" refers to the structural ribosomal RNA (rRNA) of the large component, or large subunit of eukaryotic cytoplasmic ribosomes, and thus is one of the basic components of all eukaryotic cells.

A "biological sample" suitable for use in the method for detecting a RIP II toxin, e.g. ricin (the first mode) refers to fluids such as blood, serum, saliva, urine, semen, bronchioalveolar lavage fluid, ascitic fluid or nasal lavage fluid. The biological sample may be a "clinical sample" i.e. a biological sample obtained for clinical purposes, namely for analyzing exposure to RIP II intoxication of a mammal, in particular human. A clinical sample may be of a small volume of fluid and may be fresh or frozen.

The term "incubating" used herein refers to bringing together and maintaining a biochemical system e.g. a biological sample or clinical sample with a substrate (e.g. a composition comprising 28S rRNA) under specific conditions in order to promote a particular reaction.

The term "composition comprising 28S rRNA" refers to a composition that comprises 28S rRNA and serves as a substrate for the activity of a RIP II family toxin that is putatively present in a biological or clinical sample. Non limiting examples of compositions comprising 28S rRNA include but are not limited to reticulocyte lysate, isolated ribosomal preparations or intact cells from which RNA can be extracted and analyzed. Reticulocyte lysate is commercially available, for instance, from Promega Corp.

As used herein the term "isolating RNA" refers to extracting or purifying an intact "RNA sample" from a lysate or from the cytosol of a cell originating in a biological/clinical sample of interest. Several techniques and commercially available products are known in the art in order to perform RNA isolation such as RNeasy mini kit (QIAGEN). Preferably the isolated RNA sample is a total RNA sample.

As used herein, the term "reverse transcriptase" (RT) refers to an enzyme used to generate complementary DNA (cDNA) from an RNA template, a process termed "reverse transcription" or "reverse transcriptase reaction". This type of enzyme originates in nature, mainly from retroviruses that convert single-stranded genomic RNA into double-stranded cDNA. Reverse transcription is widely used in laboratory to convert RNA into a "cDNA transcript". Methods of reverse transcribing RNA into cDNA are well known and described for example in Sambrook et al., Molecular Cloning, A Laboratory Manual, Cold Spring Harbor Laboratory Press, Cold Spring Harbor, N.Y. (2001). Reverse transcriptase enzymes are commercially available for example M-MLV (Moloney Murine Leukemia Virus) Reverse Transcriptase (e.g. by Promega) or AMY (Avian Myeloblastosis Virus) Reverse Transcriptase (e.g. by Promega).

The term "primer" as used herein refers to an oligonucleotide, which is capable of acting as a point of initiation of nucleic acid synthesis when placed under suitable conditions. Synthesis of a primer extension product, being a nucleic acid which is complementary to a template strand, is induced in the presence of nucleotides and an agent for polymerization, such as a DNA polymerase enzyme or Reverse transcriptase enzyme, at a suitable temperature and pH. Primers used in this invention may be comprised of naturally occurring dNTP, modified nucleotides, or non-natural nucleotides. Primers may also include ribonucleotides. Primers must be sufficiently long to prime the synthesis of extension products in the presence of the agent for polymerization. The exact length of the primers will depend on many factors, including temperature, application, and source of primer and would regularly be within the range of 15-45 nucleic acid bases. In one specific embodiment the primer would consist of about 25 nucleic acid bases. The location of the primer would be 40-200 bases upstream of the ricin depurination target site. In one embodiment the reverse transcriptase primer comprises the sequence CAGT-CATAATCCCACAGATGGTAGC (SEQ ID NO: 1).

Complementary nucleic acid molecules are molecules having a sequence that allows their pairing and hybridization. With respect to primers or probes the term "complementary" is used herein to mean that these molecules have a sufficient amount of complementary nucleic acids to hybridize selectively to a target nucleic acid sequence under designated conditions. The term "complementary" encompasses the terms "substantially complementary" and "perfectly complementary", preferably perfectly complementary. The rules of base pairing (or nucleotide pairing) in RNA are:

U (Uracil)—A (Adenine)

G (Guanine)—C (Cytosine)

As used herein the term "hybridizing", "hybridize" or "hybridization" refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature. The detailed conditions for hybridization can be found in e.g. Sambrook et al., 2001 Molecular Cloning, A Laboratory Manual, Cold Spring Harbor Laboratory Press, Cold Spring Harbor, N.Y.

As used herein the term "3' end" or "3' terminus" designates the extremity of the DNA or RNA strand that has a hydroxyl group linked to the 3rd carbon in the sugar-ring of the deoxyribose or ribose at its terminus. The 3'-hydroxyl is necessary in the synthesis of new nucleic acid molecules as it is ligated (joined) to the 5'-phosphate of a separate nucleotide, allowing the formation of strands of linked nucleotides. The term is also used to designate directionality of the nucleic acid strand whereby the term "3'" refers to the part of the strand that is closer to the 3' end.

As used herein the term "5' end" or "5' terminus" designates the extremity of the DNA or RNA strand that has a phosphate group attached to the fifth carbon in the sugar-ring of the deoxyribose or ribose at its terminus. A phosphate group attached to the 5'-end permits ligation of two nucleotides, i.e., the covalent binding of a 5'-phosphate to the 3'-hydroxyl group of another nucleotide, to form a phosphodiester bond. The term is also used to designate directionality of the nucleic acid strand whereby the term "5'" refers to the part of the strand that is closer to the 5' end.

As used herein the term "truncated cDNA transcript" refers to the product of a reverse transcriptase reaction wherein the reverse transcriptase enzyme halts prematurely during the course of the reaction prior to completing the full RT reaction throughout the nucleic acid template. The generated truncated cDNA transcript is therefore shorter than the expected cDNA transcript. Reverse transcriptase enzymes may stop during the course of the reaction due to several reasons, for example the reaction may stop because a nucleotide is missing in the RNA template (e.g., as a result of depurination), or because of secondary structures formed in the RNA template that disturb free reverse transcriptase enzyme movement on the RNA template. In the context of the present invention the presence of a RIP II family toxin is evidenced by the appearance of truncated cDNA transcripts that result from the depurination activity of the toxin on the 28S rRNA.

As used herein the term "labeling" refers to adding an element/tag to a molecule of interest in order to make it traceable/detectable. In the context of the invention, the truncated cDNA transcript will become detectable upon connection/ligation with a synthetic DNA strand.

As used herein the term "ligating" refers to joining two separate nucleic acid sequences. The ligation can be performed using for example, a ligating enzyme e.g. a ligase. For example, a DNA ligase, which is a specific enzyme that facilitates the joining of DNA strands together by catalyzing the formation of a phosphodiester bond, a reaction that is referred to as a "ligation reaction".

In the context of the present invention a synthetic nucleic acid strand is ligated at the 3' end of the truncated cDNA transcript to form a chimeric ligation product. The ligation is facilitated and rendered specific by performing the reaction in the presence of a dual oligonucleotide.

As used herein the term "synthetic nucleic acid strand" refers to a nucleic acid sequence that does not appear in the genomic DNA of the organism from which the biological sample/clinical sample was extracted. The synthetic nucleic acid strand is thus synthesized and provided artificially to comply with the methods or the kit of the invention. The nucleic acid may be DNA, or PNA (peptide nucleic acids). In one embodiment, the synthetic nucleic acid strand is a synthetic DNA strand. The length of the synthetic nucleic acid strand may be of about 30 to about 150 bases. The length of the synthetic nucleic acid strand is determined so that it is long enough to complement a primer and an adjacent probe, and not too long so that the real time PCR reaction would not be hampered. In one embodiment the synthetic DNA strand is of about 37 nucleotides. In one specific embodiment the synthetic strand is of the sequence 5-AAATTTTTCCGGTCGATCGCGCCGAATT-TAAGCATTG-3 denoted in SEQ ID NO: 2.

As used herein the term "chimeric ligation product" refers to the nucleic acid sequence resulting from the connection (e.g. ligation) of the synthetic nucleic acid strand and the truncated cDNA transcript, as described above. According to the methods or the kit of the invention, both strands i.e. the synthetic nucleic acid strand and the truncated cDNA transcript are brought in close proximity by incubation with a specific DNA oligonucleotide (also termed herein "dual oligonucleotide") and are subsequently ligated or linked together, thereby forming the chimeric ligation product.

As used herein the term "DNA oligonucleotide" (also termed herein "dual oligonucleotide") refers to a single-stranded DNA molecule whose sequence is able to hybridize with the 5' end of the synthetic nucleic acid strand and the 3' end of the truncated cDNA transcript. The dual oligonucleotide is composed of two nucleic acid sequence elements positioned in a sequential manner, a first of the two nucleic acid sequence elements is complementary to the 5' end of the synthetic nucleic acid strand and a second of the two nucleic acid sequence elements is complementary to the 3' end of the truncated cDNA transcript. Hybridization of the dual oligonucleotide with the synthetic nucleic acid strand and the truncated cDNA transcript juxtaposes these molecules in close proximity and allows their subsequent specific connection, for example by a ligation reaction thereby producing the chimeric ligation product described above. The dual oligonucleotide of the invention is thus synthesized and provided artificially. The sequence of the dual oligonucleotide is thus a reflection of the sequence of the 3' end of the truncated cDNA transcript and the sequence of the 5' end of the synthetic nucleic acid strand. The length of the dual oligonucleotide may be from about 20 to about 40 nucleic acid bases, about half of which are complementary to nucleic acid bases of the truncated cDNA and about half to nucleic acid bases of the synthetic strand. In one embodiment the dual oligonucleotide is of about 26 nucleotides in length. In certain embodiments the dual oligonucleotide is of the sequence 5-XXXXXXXXXXXXTTGAG-GAACCGCAG-3 denoted in SEQ ID NO. 7, wherein X represents independently any nucleic acid A, T, G, C in a sequence which corresponds to the 5' of the synthetic nucleic acid strand used in the reaction. In one specific embodiment the dual oligonucleotide is of the sequence 5-CCG-GAAAAATTTTTGAGGAACCGCAG-3 denoted in SEQ ID NO: 3.

As used herein the term polymerase chain reaction ("PCR") refers to a technique for in vitro amplification of specific DNA sequences, allowing small quantities of short sequences to be detected and/or analyzed. Measurements of the amounts of target nucleic acids may also be performed using quantitative real time PCR.

As used herein the term "quantitative real time PCR" refers to a laboratory technique based on the polymerase chain reaction (PCR), monitoring the amplification of a targeted DNA molecule, e.g. the chimeric ligation product, during the PCR, i.e. in real-time but also quantitatively. Two common methods for the detection of PCR products in real-time PCR are: (1) use of non-specific fluorescent dyes that intercalate with any double-stranded DNA, and (2) sequence-specific DNA probes consisting of oligonucleotides that are labelled with a fluorescent reporter which permits detection only after hybridization of the probe with its complementary sequence.

As used herein the term "amplifying" refers to increasing the number of copies of a DNA or RNA sequence of interest, such as the chimeric ligation product described above.

As described above the detection method of the invention can be employed also to detect exposure to RIP II family toxins by detecting ribosomal damage. Therefore, in another one of its aspects, which corresponds to the second mode described above, the present invention provides a method for detecting ribosomal damage induced by exposure to RIP II family toxins in a biological sample, the method comprising the steps of:

a. Isolating RNA from a biological sample, wherein the isolated RNA comprises 28S rRNA;

b. Performing a reverse transcriptase (RT) reaction using a primer complementary to a sequence of the 28S rRNA which is positioned 3' to the RIP II family enzyme depurination site, whereby a truncated cDNA transcript is formed if the rRNA was exposed to a RIP II family toxin and was depurinated;

c. Labeling said truncated cDNA transcript obtained in step (b) by ligating a synthetic nucleic acid strand at the truncated 3' end of the transcript, thereby obtaining a chimeric ligation product; and d. Amplifying the chimeric ligation product using PCR;

wherein detection of an amplified chimeric ligation product indicates the presence of ribosomal damage induced by exposure to RIP II family toxins in said biological sample.

As used herein the term "ribosomal damage" refers to an alteration in ribosomal structure leading to ribosomal malfunction, specifically the production of non-functional proteins or cessation of protein production. In the context of the invention, ribosomal damage particularly refers to the depurination event described above which is a result of a subject's exposure to RIP II family toxins.

As used herein the term "exposure" refers to an intoxication of a subject with a RIP II family toxin in an amount that results in ribosomal damage.

A "biological sample" suitable for use in the method for detecting ribosomal damage induced by exposure to RIP II family toxins, e.g. ricin (the second mode) refers to a fluid (such as blood, serum, saliva, urine, semen, bronchoalveolar lavage fluid, ascitic fluid, nasal lavage fluid), intact cells (such as cells obtained by scraping of nasal cavities, palate, cheek or skin) or extracts thereof, or tissue samples. The biological sample may be a "clinical sample" i.e. a biological sample obtained for clinical purposes, namely for analyzing exposure to RIP II intoxication of a mammal, in particular human. A clinical sample may be of a small volume and includes fluid, cell or tissue specimens. The fluid, cell or tissue specimen may be fresh or frozen.

In one embodiment, the methods of the invention (both the first and the second modes of detection) may include a step of opening the rRNA secondary structure in the isolated RNA prior to performing the reverse transcriptase step.

As used herein the term "rRNA secondary structure" refers to the base-pairing interactions within the same ribosomal RNA molecule. Since an RNA molecule is single stranded, it often forms complicated intramolecular base-pairing interactions. Although, the secondary structures of ribosomal RNA are functional and linked to the role of ribosomes in transcription, they may interfere with a smooth gliding of the reverse transcriptase on its RNA template and may at times cause premature halt of the enzymatic activity potentially resulting in short cDNA transcripts that are non-related to the depurination effect of a RIP II toxin. In order to overcome this potential disturbance the secondary RNA structure may be opened prior to the RT reaction.

As used herein, the term "opening the rRNA secondary structure", or "melting the rRNA secondary structure" refers to breaking the secondary structure of the 28S rRNA molecule and thus enabling linearization of the RNA molecule in order to facilitate the unobstructed gliding of the reverse transcriptase on the RNA molecule, and thereby minimize non-specific halting of the enzyme's activity.

Opening or melting the rRNA secondary structure can be performed using any method known in the art, for example denaturation with formamide, glyoxal or DMSO. In one embodiment the opening is facilitated by increasing the temperature of the reaction, e.g. to be in the range of 50° C. to 75° C., such as about 60° C., or about 65° C., and adding DMSO to the reaction. Determining the suitable concentration of DMSO is well within the knowledge of a person skilled in the art and is within the range of 3%-10% DMSO volume/volume. In one specific embodiment, DMSO is added at a concentration of 5%.

In such case, that the reaction is performed at an increased temperature, the RT enzyme that is selected for performing the reaction, is a thermostable RT enzyme.

As used herein the term "thermostable reverse transcriptase (RT) enzyme" refers to a reverse transcriptase enzyme which is fully enzymatically active at higher temperatures than conventional enzymes e.g. above 60° C., for example active at 65° C. One non-limiting example of such an enzyme is the eAMV (enhanced Avian Myeloblastosis Virus) reverse transcriptase enzyme (Sigma Aldrich).

As used herein the term "buffers for performing each of the reactions" refers to a solution which provides optimal pH conditions for an enzyme to function properly. In the kit of the invention, buffers for the Reverse transcriptase, the ligase and the DNA polymerase may be optionally provided.

As used herein the term "DNA target probe with a fluorescent reporter at the 5' end and a quencher of fluorescence at the 3' end" refers to a DNA probe employed for quantitative RT-PCR, that is able to hybridize with the DNA dual probe and possesses a fluorescent reporter at its 5' end and a quencher of fluorescence at the 3' end. This DNA target probe will provide a fluorescent signal only upon binding to the PCR product of interest.

Figures 1C, 1D:
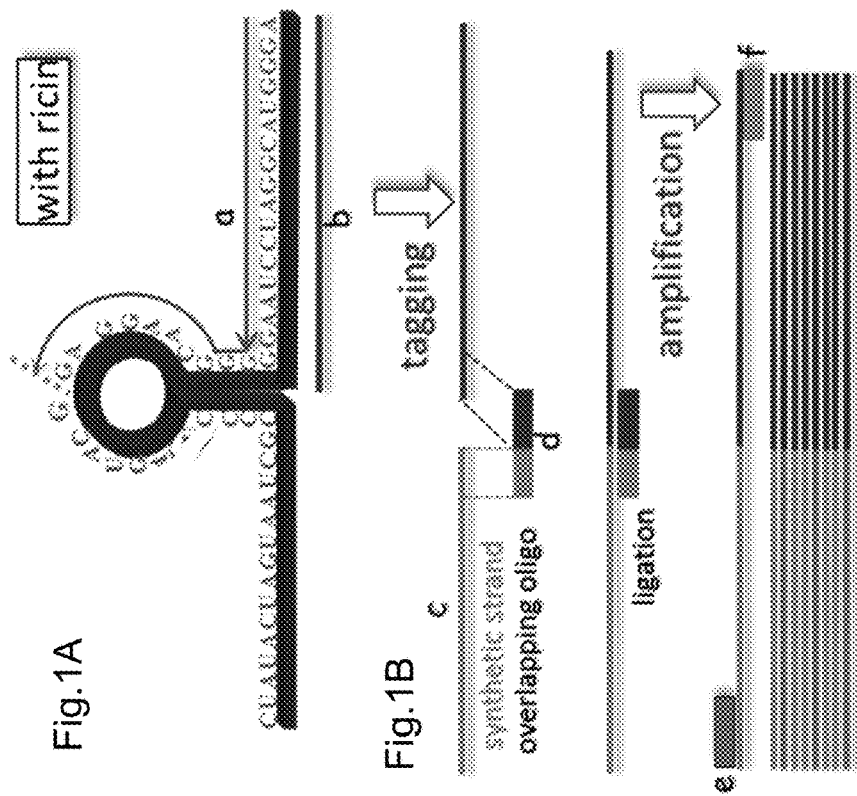

One embodiment of the invention is schematically shown in FIG. 1. FIG. 1A, shows the 28S rRNA ricin target-site region after depurination by ricin. FIG. 1C shows the same area without exposure to ricin. As can be seen in FIG. 1A, adenine residue was removed by ricin in the GAGA target sequence (highlighted). Reverse transcription of this ribosomal area will result in different transcripts depending on exposure to ricin. Due to the missing A residue (site of depurination is shown by a dotted line) in rRNA that was exposed to ricin, reverse transcription will halt at the site of depurination thus giving rise to a truncated cDNA product. This truncated product is marked by the line "b" (which is only a representation and does not reflect the actual length of the transcript).

Subsequently, as can be seen in FIG. 1B, the truncated cDNA product is tagged by incubation with two nucleic acid molecules: 1. a non-homologous (heterogeneous) synthetic DNA strand (namely having a sequence which does not interact with the rRNA sequences, shown in the figure as c) and 2. a DNA oligonucleotide (also termed herein a "dual oligonucleotide", shown in the Figure as d) whose sequence complements in-tandem that of the 5' end of the non-homologous synthetic DNA strand and the 3' end of the truncated cDNA product. The DNA oligonucleotide (i.e. the dual oligonucleotide) juxtaposes the synthetic strand and the truncated cDNA product. The two molecules are then annealed by ligation with DNA ligase. The chimeric ligation product is then incubated with 2 primers complementing respectively the synthetic DNA (e) and the truncated cDNA product (f) sequences and then amplified by quantitative Real Time PCR (qRT-PCR).

In the absence of ricin, as schematically presented in FIG. 1C, reverse transcription from the 28S rRNA ricin target-site region is expected to continue unimpeded (g), to give rise to a long cDNA product (h). Since the DNA oligonucleotide (the dual oligonucleotide) complements an internal sequence (denoted by parallel dotted lines) within the long cDNA product generated in the absence of ricin, the chimeric ligation product is not expected to form and amplification will not occur (FIG. 1D).

Due to the unique secondary structure of the 28S rRNA template, rare events of RT polymerase fall-off at this region may occur resulting in formation of truncated cDNA products, even in the absence of ricin. The outcome of the RT reaction (even in the absence of ricin intoxication) is thus composed of mostly long cDNA products and low levels of truncated transcription product. Amplification of the truncated transcription products during the qRT-PCR step, may lead to false positive results.

In order to eliminate the false positives, namely to eliminate the occurrence of non-relevant short transcripts (those that are not generated by the depurination effect of ricin, but rather by the spontaneous fall-off of the reverse transcriptase), a step of melting the secondary structure of the template is performed.

Therefore, in one embodiment, the method of the invention further comprises a step of "melting" of the secondary structure of the RNA template. The melting step may be performed by any means known in the art to affect secondary structure of nucleic acids. In one non-limiting embodiment, the method comprises adding dimethyl sulfoxide (DMSO) at the initial step of the reverse transcriptase reaction and performing the reverse transcription at an elevated temperature, e.g. 65° C. In such case the reverse transcriptase enzyme which is selected for use in the reaction is stable and active at high temperatures. In one specific embodiment the enzyme is eAMV reverse transcriptase (e.g. from Sigma-Aldrich). This embodiment of the invention is schematically presented in FIG. 2.

The basic assay conditions are shown in FIG. 2A: while using a common reverse transcriptase (e.g. MLV-RT) mostly long cDNA products are generated (as shown in (b)) due to the unique secondary structure of the 28S rRNA template, rare events of RT polymerase fall-off at this region occur resulting in formation of truncated cDNA products (shown in (c)). The net result is thus composed of long cDNA products (d) and low levels of truncated transcription products (e). Amplification of the truncated transcription products during the qRT-PCR step, leads to false positive results (as shown in (f)).

The assay conditions including the melting step are shown in FIG. 2B: "melting" of secondary structure of RNA template by adding dimethyl sulfoxide (DMSO) and by performing reverse transcription at elevated temperature, 65° C. with a more thermostable reverse transcriptase, e.g. the RT-eAMV enzyme, results in generation of long transcription products (h). Since no truncated transcription products are generated (in the absence of ricin) no ligation to the synthetic DNA strand occurs and no amplification product is generated. Namely, the occurrence of false positives is minimal to none.

As indicated above, in one aspect, the method of the invention is used to identify the presence of the toxin, e.g. ricin in a clinical sample obtained from a subject. This embodiment is schematically represented in FIG. 3A. The clinical sample is incubated with reticulocyte lysate, followed by extraction of the reticulocyte lysate RNA and its analysis for the presence of the unique truncated cDNA product, according to the method of the invention.

In another aspect, the method of the invention is used to identify exposure to toxin, by measuring ribosomal damage in the subject's cells or free circulating RNA. This embodiment is schematically represented in FIG. 3B. The subject's RNA is analyzed for the presence of unique truncated cDNA product, according to the method of the invention.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Experimental Procedures

List of Abbreviations

RT=Reverse Transcription
PCR=Polymerase Chain Reaction
qRT-PCR=quantitative Real-Time PCR
RNA=Ribonucleic Acid
DNA=Deoxyribonucleic acid
rRNA=ribosomal RNA
cDNA=complementary DNA
DMSO=Dimethyl sulfoxide
dNTP=Deoxynucleoside triphosphate
DTT=Dithiothreitol
BSA=Bovine Serum Albumin
FAM=6-carboxyfluorescein
BHQ=Black Hole Quencher®
PBS=phosphate buffered saline 1) RNA Isolation RNA was isolated from the biological sample or from the reticulocyte lysate preparation following its incubation for 2 hours at 37° C. with the biological sample, using a commercial kit—Rneasy mini kit (QIAGEN) according to the manual's instructions. The isolated RNA was divided into aliquots and stored at −70° C.

Quantification of RNA was performed using a QUBIT (Invitrogen) instrument, together with the QUBIT RNA HS assay kit (Molecular Probes).

2) RT Reaction:

2.1 Denaturation and Annealing:

The followings were added to a PCR tube:

```
1 µl of DMSO

1 µl of Primer R1 (5-CAGTCATAATCCCACAGATGGTAGC-3)
(SEQ ID NO: 1) at a concentration of 5 pmole/µl Water (Water for molecular biology, Sigma) to
complete a volume of 10.5 µl.
```

The PCR tube was introduced into a PCR thermal cycler device with the following program:

3 min at 90° C., 2 min at 4° C.

2.2 RT

RT (eAMV)

The following are added to the PCR tube:

2 µl of dNTPs (5 mM)
1 µl of DTT (100 mM)
1 µl of RNasin plus (Promega)
2 µl of BSA (10 mg/ml)
2 µl of eAMV buffer (×10)
1.5 µl of RT-eAMV enzyme The PCR tube was introduced into a PCR thermal cycler device with the following program:

50 min at 65° C., 2 min at 4° C.

2.3 Purification of cDNA using columns of DTR gel filtration cartridges (edgeBio) and centrifugation (3 min, 850×g)

3) Ligation Reaction 3.1 Production of the Hybrid

The following were added to a PCR tube:

```
50 µl of Synthetic oligonucleotide
(5-AAATTTTTCCGGTCGATCGCGCCGAATTTAAGCATTG-3) (SEQ
ID NO: 2) at a concentration of 10⁹ copies/µl.

50 µl of the dual oligonucleotide
(5-CCGGAAAAATTTTTGAGGAACCGCAG-3) (SEQ ID NO: 3)
at a concentration of 10⁹ copies/µl.
```

The PCR tube was introduced into a PCR thermal cycler device with the following program:
0.5 min at 90° C., 2 min at 50° C., 2 min at 30° C.

3.2 Ligation of the Hybrid and the RT Product of Step 2 (the cDNA)

The followings were added to a PCR tube:
5 µl of the solution containing the hybrid produced in step 3.1
5 µl of Taq DNA reaction buffer (×10, Biolabs)
2 µl of Taq DNA ligase (Biolab)
13 µl of Water for molecular biology (Sigma)
15 µl of cDNA (produced by RT reaction)

The PCR tube was introduced into a PCR thermal cycler device with the following program:
60 min at 45° C., 2 min at 4° C.

4) Quantitative Real-Time PCR Reaction

The followings were added to a PCR tube:

```
25 µl of Sensifast mix (Life gene)

4 µl of Primer F (5-CAATGCTTAAATTCGGCGCGA-3) (SEQ
ID NO: 4) at a concentration of 5 pmole/µl 4 µl of Primer R2 (5-TTCGCCCCATTGGCTCCT-3) (SEQ
ID NO: 5 at a concentration of 5 pmole/µl 2 µl of Probe 2 (FAM-5-CCGGAAAAATTTTTGAG GAACCGCA
GG-3 BHQ) (SEQ ID NO: 6) at a concentration of
5 pmole/µl 20 µl of cDNA after ligation (as obtained in
step 3).
```

The PCR tube was introduced into a 7500 real-time PCR system (Applied Biosystems) device with the following program:
60 s at 95° C., and 50 cycles of 15 s at 95° C. and 35 s at 60° C.

The results were analyzed using the Auto Baseline function to determine the Critical Threshold (Ct). If Ct<50, the sample was considered positive for the presence of the toxin.

If Ct=undetected the result is negative.

Example 1

Detection of Ricin-Induced Truncated cDNA Following Incubation of Different Amounts of Ricin in Reticulocyte Lysate, Using a Common Reverse Transcriptase.

Purified ricin [Gal et al., 2014, Toxicol. Rep. 1:495-504] was added to reticulocyte lysates at final concentrations of 0.5-50 ng/ml and incubated at 37° C. for 2 hours. Following tagging and reverse transcription with the reverse transcriptase MLV RT, the RT products were amplified and analyzed by qRT-PCR [For performing the RT reaction, the following components were added to the PCR tube: 2 µl of dNTPs (5 mM), 1 µl of DTT (100 mM), 1 µl of RNasin plus (Promega), 2 µl of BSA (10 mg/ml), 2 µl of MLV buffer (×10) and 1.5 µl of RT-MLV enzyme. The PCR tube was introduced into a PCR thermal cycler device with the following program: 45 min at 40° C., 2 min at 4° C. No DMSO was used in the denaturation and annealing step that precedes the RT reaction]. As shown in FIG. 4, these results demonstrate that under these conditions, ricin-dependent truncated cDNA copies can be detected at ricin concentrations as low as 0.5 ng/ml, however false-positive results were observed as well (samples with no ricin displayed a positive signal).

Example 2

Detection of Ricin-Induced Truncated cDNA Following Incubation of Different Amounts of Ricin in Reticulocyte Lysate, Using a Thermostable Reverse Transcriptase.

Figure 5:
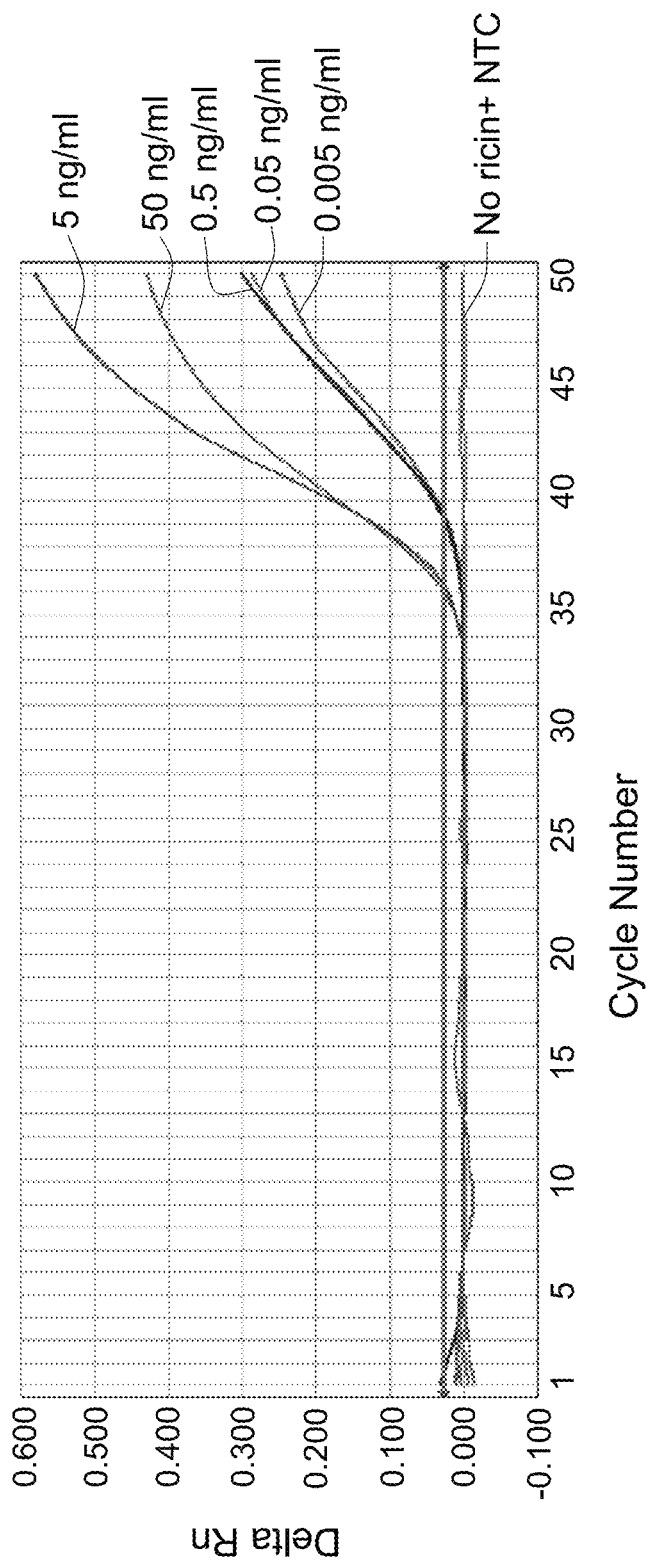

Purified ricin was added to reticulocyte lysates at final concentrations of 0.005-50 ng/ml and incubated at 37° C. for 2 hours. Reverse transcription was performed according to the protocol schematically represented in FIG. 2B, utilizing heat-resistant eAMV RT. Reverse transcription products were amplified and analyzed by qRT-PCR (see FIG. 5). These results demonstrate that under these specific conditions, ricin-dependent truncated cDNA copies can be detected even when ricin concentrations were as low as 5 pg/ml, without false-positive results (samples with no ricin are negative).

Example 3

Detection of Ricin in Broncheoalveolar Fluid (BALF) of Pulmonary-Exposed Animal Models The assay of the invention can be applied in two different modes to identify exposure to ricin. In the first mode the assay detects the presence of ricin in a clinical sample by measuring its enzymatic activity on an rRNA substrate, e.g. on reticulocyte lysate. In the second mode, the assay detects the presence of damaged rRNA resulting from ricin intoxication. This is achieved by extracting RNA from biological samples and subjecting the extracted RNA to the assay of the invention, thus determining the existence of RNA damage which is an indicator of ricin intoxication.

The first mode is represented in FIG. 3A, accordingly, clinical samples harvested from the subject are assayed directly for the presence of ricin toxin. This is achieved by incubating the sample with reticulocyte lysate, followed by extraction of the reticulocyte lysate RNA and its analysis for the presence of truncated cDNA product. This mode of application allows one to determine the presence of active ricin toxin in the clinical sample.

The second mode is represented in FIG. 3B, clinical samples harvested from the subject are assayed for host ribosomal damage. This is achieved by either harvesting host cells from various clinical samples or by withdrawing a blood sample, followed by extraction of either host cell RNA or circulating cell-free RNA, respectively, and its analysis for the presence of truncated cDNA product. This mode of application allows one to determine that ribosomes of the subject have been impaired by the action of ricin toxin.

Figure 6:
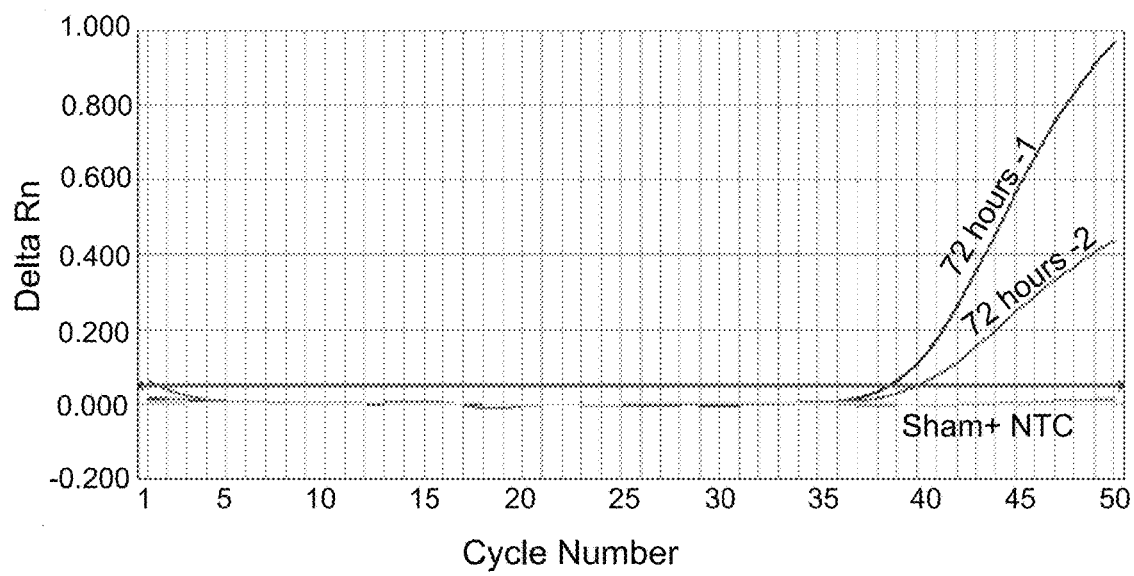

In order to measure ricin intoxication in vivo, mice were exposed to a lethal dose of ricin by the intranasal (IN) route and BALF was collected 72 hours later by instillation of 1 ml PBS. The BALF was screened for the presence of enzymatically-active ricin by monitoring the generation of truncated 28S rRNA cDNA products in a reticulocyte lysate preparation, see FIG. 6. In this example the ricin was detected according to the first mode described above (namely, detection of the presence of the toxin itself in the sample). The BALF sample was incubated in reticulocyte lysate for 2 hours as described in Experimental procedures (1). Only the reticulocyte RNA is extracted, since the amount of RNA from the biological sample is negligible and thus does not cause any effect on the assay. Results are shown for two mice (72 hours-1 and 72 hours-2). This experiment shows that enzymatically active ricin can be detected in the lungs of mice, even at 72 hours after exposure to the toxin, by applying the method described in the present invention.

Figure 7:
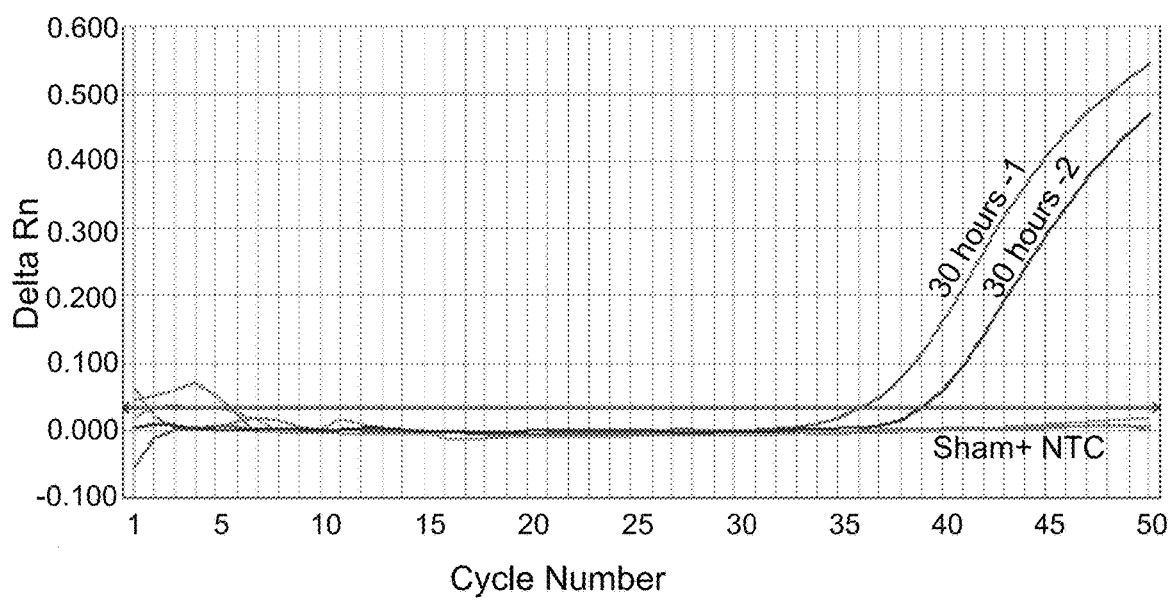

Next, swine were exposed to a lethal dose of ricin by the intratracheal (IT) route and BALF was collected 30 hours later by instillation of 30 ml PBS. The BALF was screened for the presence of enzymatically-active ricin by monitoring the generation of truncated 28S rRNA cDNA products in a reticulocyte lysate preparation, see FIG. 7. Results are shown for two swine (30 hours-1 and 30 hours-2). This experiment shows that enzymatically active ricin can be detected in the lungs of swine, even at 30 hours after exposure to the toxin, by applying the method described in the present invention.

Example 4

Detection of Ricin-Induced Ribosomal Damage in Bronchioalveolar Fluid (BALF) of Pulmonary-Exposed Animal Models In this example the ricin intoxication was determined by detecting ricin-induced ribosomal damage in the biological sample, according to the second mode described above.

Figure 8:
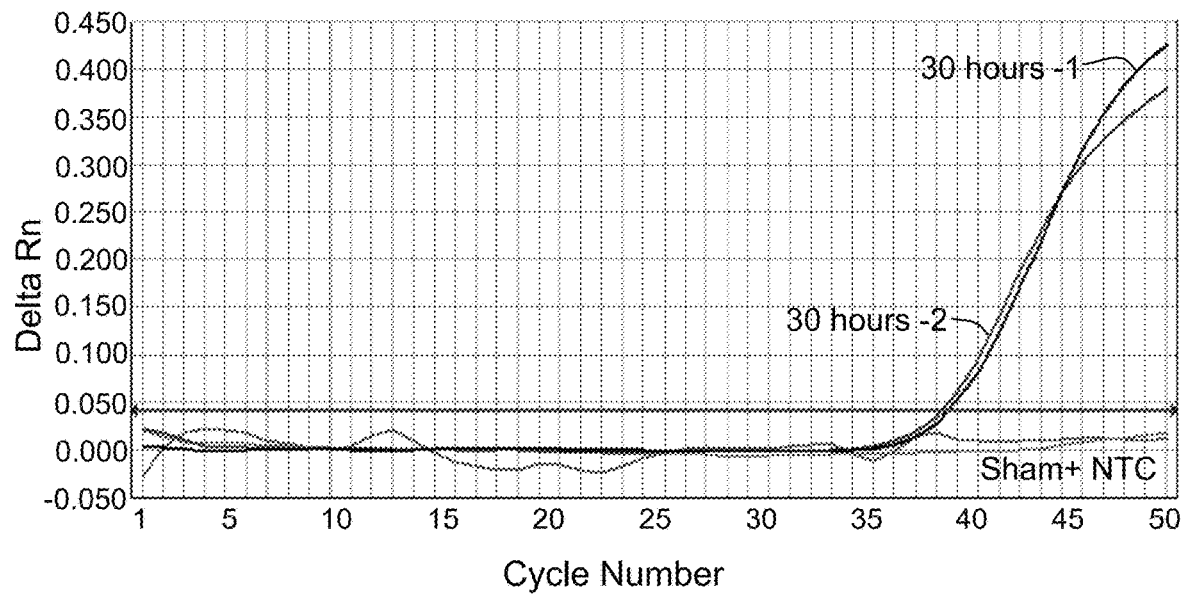

Swine were exposed to a lethal dose of ricin by the intratracheal (IT) route and BALF was collected 30 hours later. Cells were harvested from the BALF and RNA extracted from these cells was screened for ricin-induced ribosomal damage by monitoring the generation of truncated 28S rRNA cDNA products, see FIG. 8. Results are shown for two swine (30 hours-1 and 30 hours-2). This experiment shows that ricin-induced ribosome damage can be detected in cells isolated from BALF collected from swine, even at 30 hours after exposure to the toxin, by applying the method described in the present invention.

Example 5

Figure 9:
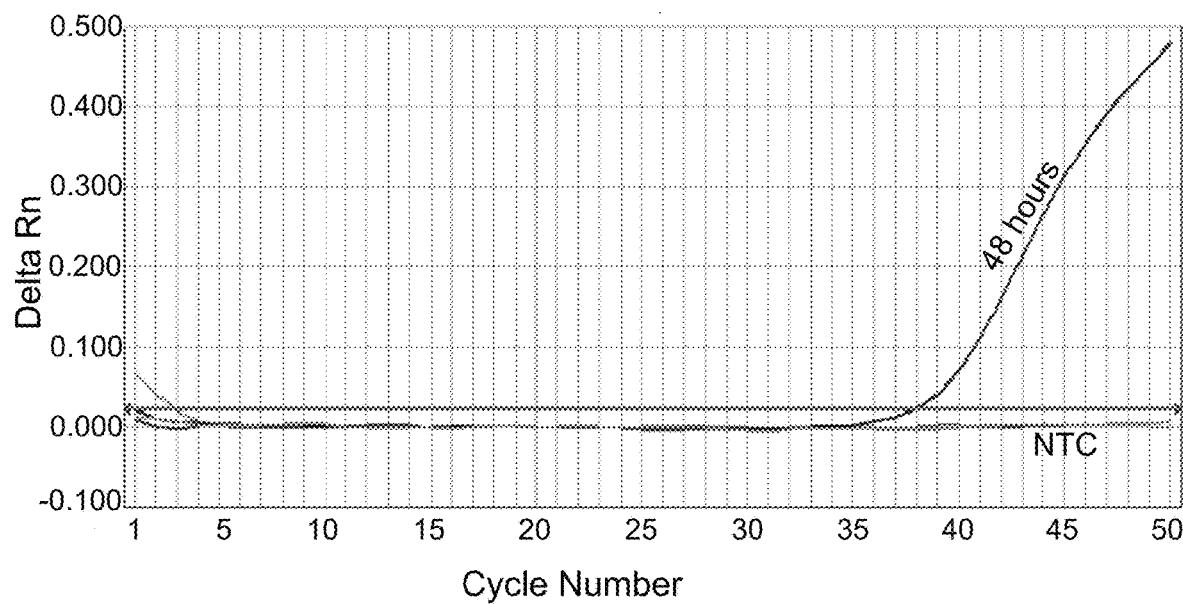

Detection of Ricin Exposure in Cells Harvested from the Ascitic Fluid of Systemically Intoxicated Animal Models Mice (n=10) were exposed to a lethal dose of ricin by the intraperitoneal (IP) route and ascitic fluid was harvested 48 hours later. Cells were harvested from the pooled ascitic fluids and RNA extracted from these cells was screened for ricin-induced ribosomal damage by monitoring the generation of truncated 28S rRNA cDNA products, see FIG. 9. This experiment shows that ricin-induced ribosome damage can be detected in cells isolated from ascitic fluid of mice even at 48 hours after exposure to the toxin, by applying the method described in the present invention.

Figure 10:
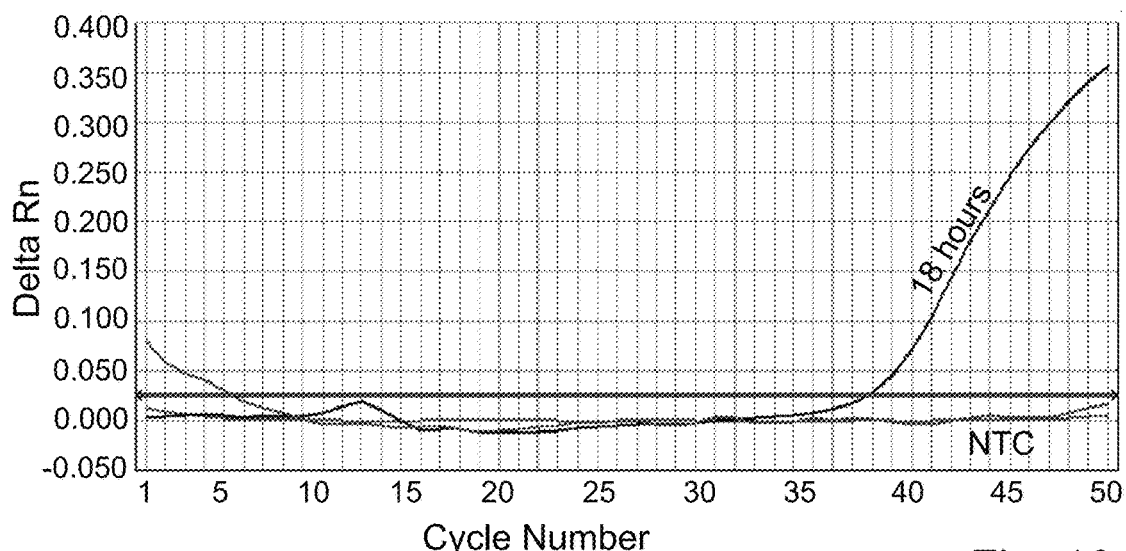

Following, a swine was exposed to a lethal dose of ricin by the intraperitoneal (IP) route and ascitic fluid was harvested 18 hours later. Cells were harvested from the ascitic fluid and RNA extracted from these cells was screened for ricin-induced ribosomal damage by monitoring the generation of truncated 28S rRNA cDNA products, see FIG. 10. This experiment shows that ricin-induced ribosome damage can be detected in cells isolated from ascitic fluid of swine, even at 18 hours after exposure to the toxin, by applying the method described in the present invention.

Example 6

Detection of Ricin Exposure in Serum of Systemically Intoxicated Animal Models

Figure 11:
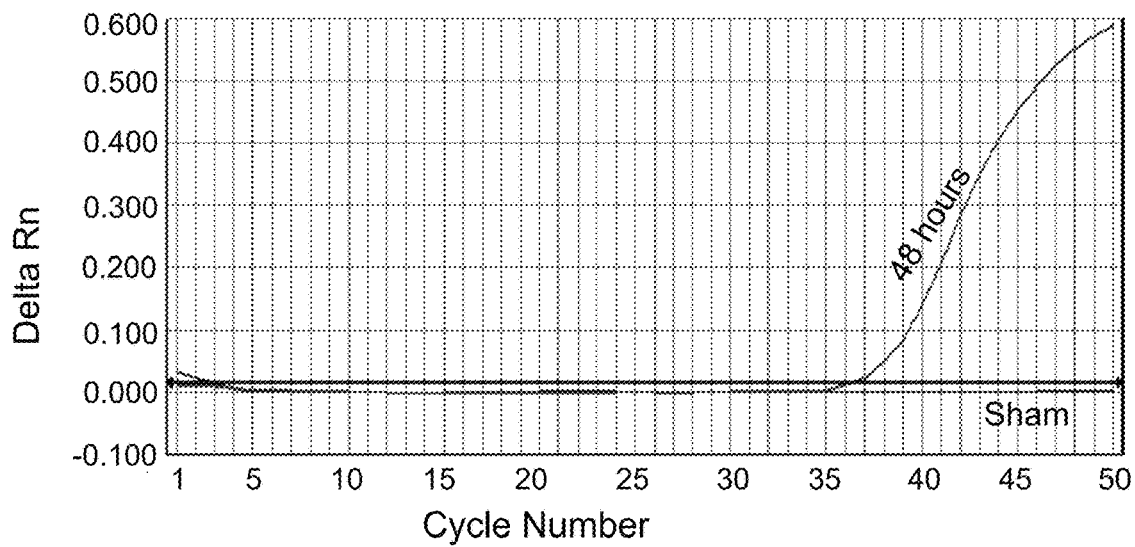

Mice (n=10) were exposed to a lethal dose of ricin by the intraperitoneal (IP) route and blood samples were withdrawn 24 hours later. Cell-free RNA was extracted from the pooled sera and screened for ricin-induced ribosomal damage by monitoring the generation of truncated 28S rRNA cDNA products, see FIG. 11. This experiment shows that ricin-induced ribosome damage can be detected in blood samples of mice collected at 24 hours after exposure to the toxin, by applying the method described in the present invention.

Figure 12:
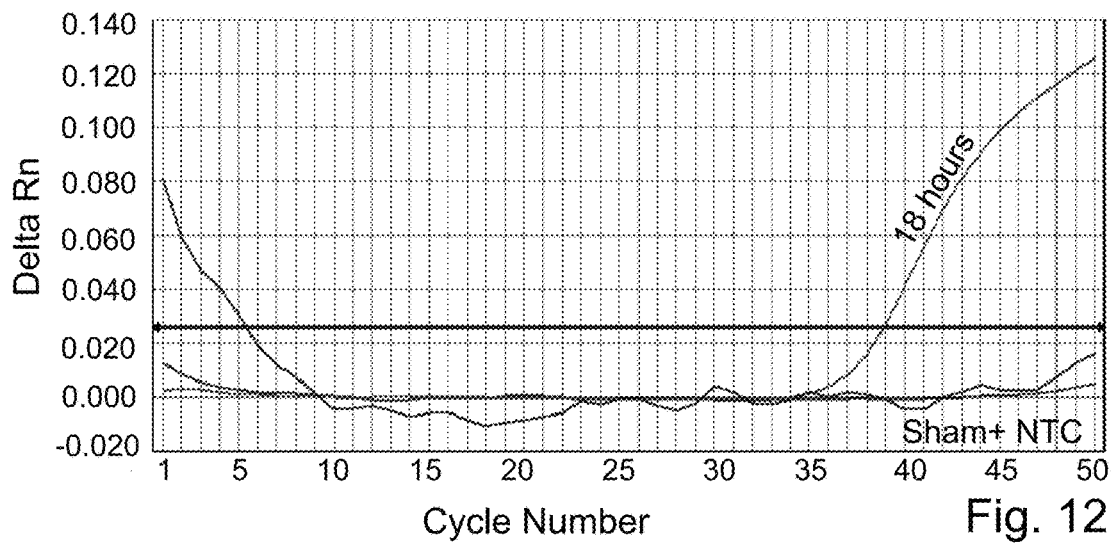

Following, a swine was exposed to a lethal dose of ricin by the intraperitoneal (IP) route and a blood sample was withdrawn 18 hours later. Cell-free RNA was extracted from the serum and screened for ricin-induced ribosomal damage by monitoring the generation of truncated 28S rRNA cDNA products, see FIG. 12. This experiment shows that ricin-induced ribosome damage can be detected in blood samples of swine collected at 18 hours after exposure to the toxin, by applying the method described in the present invention.

| | | Sequence listing | | |
|---|---|---|---|---|
| SEQ ID NO | | Sequence (5' to 3') | Name | Type |
| SEQ ID NO: 1 | | CAGTCATAATCCCACAGATGGTAGC | Primer-R1 | DNA |
| SEQ ID NO: 2 | | AAATTTTTCCGGTCGATCGCGCCGAATTTAAGCATTG | Synthetic oligonucleotide | DNA |
| SEQ ID NO: 3 | | CCGGAAAAATTTTGAGGAACCGCAG | dual oligonucleotide | DNA |
| SEQ ID NO: 4 | | CAATGCTTAAATTCGGCGCGA | Primer-F | DNA |
| SEQ ID NO: 5 | | TTCGCCCCATTGGCTCCT | Primer-R2 | DNA |
| SEQ ID NO: 6 | | CCGGAAAAATTTTGAGGAACCGCAGG | Probe 2 | DNA |
| SEQ ID NO: 7 | | XXXXXXXXXXXXTTGAGGAACCGCAG | Dual probe general | DNA |

-continued

Sequence listing

| SEQ ID NO | Sequence (5' to 3') | Name | Type |
|---|---|---|---|
| SEQ ID NO: 8 | CUAUACUAGUAAUCGCCCCUC AGUACGGAGGAACGGGGGAA UCCUAGGCAUGGGA | 28S rRNA ricin target-site region after depurination by ricin | RNA |
| SEQ ID NO: 9 | CUAUACUAGUAAUCGCCCCUC AGUACGAGAGGAACGGGGGA AUCCUAGGCAUGGGA | 28S rRNA ricin target-site region | RNA |

The invention claimed is:

1. A method for detecting exposure to a RIP II family toxin in a biological sample, the method comprising the steps of:
   a. obtaining an isolated RNA preparation comprising 28S rRNA;
   b. performing a reverse transcriptase (RT) reaction using a primer complementary to a sequence of the 28S rRNA which is positioned 3' to the RIP II family enzyme depurination site, whereby a truncated cDNA transcript is formed if the 28S rRNA was exposed to a RIP II family toxin and was depurinated;
   c. labeling said truncated cDNA transcript obtained in step (b) by ligating a synthetic nucleic acid strand at the truncated 3' end of the transcript, thereby obtaining a chimeric ligation product; and
   d. amplifying the chimeric ligation product using polymerase chain reaction (PCR);
   wherein detection of an amplified chimeric ligation product indicates exposure to a RIP II family toxin.

2. The method of claim 1, wherein prior to step (a) said isolated RNA preparation comprising 28S rRNA is incubated with a biological sample obtained from a subject suspected of exposure to a RIP II family toxin.

3. The method of claim 1, wherein said isolated RNA preparation comprising 28S rRNA of step (a) is isolated from a biological sample obtained from a subject suspected of exposure to a RIP II family toxin.

4. The method of claim 1, further comprising a step of opening the rRNA secondary structure in said isolated RNA during said reverse transcriptase step.

5. The method of claim 4, wherein the reverse transcriptase (RT) reaction is performed at an elevated temperature.

6. The method of claim 5, wherein a thermostable reverse transcriptase enzyme is used in the reaction.

7. The method of claim 1, wherein said biological sample is a clinical sample.

8. The method of claim 1, wherein the RIP II family toxin is ricin.

9. The method of claim 1, wherein said ligation of a synthetic DNA strand to the truncated cDNA transcript is performed by adding to the ligation reaction a DNA dual oligonucleotide having a sequence capable of hybridizing with the 3' terminus of said truncated cDNA transcript and a consecutive sequence capable of hybridizing with the 5' terminus of said synthetic DNA strand.

10. The method of claim 1, wherein the biological sample is obtained from 1 hour to 120 hours post exposure to the RIP II family toxin.

11. A method for detecting a RIP II family toxin in a biological sample, the method comprising the steps of:
   a. incubating said biological sample with a composition comprising 28S rRNA;
   b. isolating RNA from said composition comprising 28S rRNA;
   c. performing a reverse transcriptase (RT) reaction using a primer complementary to a sequence of the 28S rRNA which is positioned 3' to the RIP II family enzyme depurination site, whereby a truncated cDNA transcript is formed if the 28S rRNA was exposed to a RIP II family toxin and was depurinated;
   d. labeling said truncated cDNA transcript obtained in step (c) by ligating a synthetic nucleic acid strand at the truncated 3' end of the transcript, thereby obtaining a chimeric ligation product; and
   e. amplifying the chimeric ligation product using polymerase chain reaction (PCR);
   wherein detection of an amplified chimeric ligation product indicates that said biological sample contains RIP II family toxins.

12. A method for detecting ribosomal damage induced by exposure to RIP II family toxins in a biological sample, the method comprising the steps of:
   a. isolating RNA from a biological sample, wherein the isolated RNA comprises 28S rRNA;
   b. performing a reverse transcriptase (RT) reaction using a primer complementary to a sequence of the 28S rRNA which is positioned 3' to the RIP II family enzyme depurination site, whereby a truncated cDNA transcript is formed if the 28S rRNA was exposed to a RIP II family toxin and was depurinated;
   c. labeling said truncated cDNA transcript obtained in step (b) by ligating a synthetic nucleic acid strand at the truncated 3' end of the transcript, thereby obtaining a chimeric ligation product; and
   d. amplifying the chimeric ligation product using PCR;
   wherein detection of an amplified chimeric ligation product indicates the presence of ribosomal damage induced by exposure to RIP II family toxins in said biological sample.

13. A kit for performing the method of claim 1, comprising:
   (a) a synthetic DNA strand;
   (b) a DNA dual oligonucleotide having a sequence capable of hybridizing with the 3' terminus of a truncated cDNA transcript of a portion of the 28S rRNA obtained by an RT reaction upon depurination by a RIP II family toxin and a consecutive sequence capable of hybridizing with the 5' terminus of said DNA synthetic strand;
   (c) DNA primers having a sequence capable of hybridizing with the 3' terminus of the synthetic DNA strand;
   (d) DNA primers having a sequence capable of hybridizing with the 5' terminus of said truncated cDNA transcript
   (e) a container; and optionally
   (f) instructions for use in detecting exposure to a RIP II family toxin in a biological sample.

14. The kit of claim 13, further comprising:
   (g) a DNA primer having a sequence capable of hybridizing with a sequence of the 28S rRNA which is positioned 3' to the RIP II family enzyme depurination site; and optionally
   (h) a reverse transcriptase enzyme; and optionally
   (i) a ligase enzyme; and optionally
   (j) DNA polymerase enzyme; and optionally
   (k) buffers for performing one or more of reverse transcriptase, ligase and DNA polymerase reactions; and optionally
   (l) dNTPs.

15. The kit of claim 13, further comprising an agent for opening the rRNA secondary structure, wherein said agent is formamide, glyoxal or Dimethyl sulfoxide (DMSO).

16. The kit of claim 15, wherein the reverse transcriptase is active at an elevated temperature.

17. The kit of claim 13, further comprising a DNA target probe with a fluorescent reporter at the 5' end and a quencher of fluorescence at the 3' end having a sequence capable of hybridizing with said DNA dual oligonucleotide.

18. The kit of claim 13, wherein the RIP II family toxin is ricin.

* * * * *

SEQUENCE LISTING

<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: Primer- R1
<220> FEATURE:
<221> NAME/KEY: misc_feature
<223> OTHER INFORMATION: Synthetic

<400> SEQUENCE: 1
cagtcataat cccacagatg gtagc                                     25

<210> SEQ ID NO 2
<211> LENGTH: 37
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Synthetic

<400> SEQUENCE: 2 aaattttttcc ggtcgatcgc gccgaattta agcattg                       37

<210> SEQ ID NO 3
<211> LENGTH: 26
<212> TYPE: DNA
<213> ORGANISM: Artificial Sequence
<220> FEATURE:
<223> OTHER INFORMATION: dual oligonucleotide
<220> FEATURE:
<221> NAME/KEY: misc_feature
<223> OTHER INFORMATION: Synthetic

<400> SEQUENCE: 3
ccggaaaaat ttttgaggaa ccgcag                                    26

<210> SEQ ID NO 4
<211> LENGTH: 21
<212> TYPE: DNA
<213> ORGANISM: Artificial Sequence
<220> FEATURE:
<223> OTHER INFORMATION: Primer-F
<220> FEATURE:
<221> NAME/KEY: misc_feature
<223> OTHER INFORMATION: Synthetic

<400> SEQUENCE: 4
caatgcttaa attcggcgcg a    21

<210> SEQ ID NO 5
<211> LENGTH: 18
<212> TYPE: DNA
<213> ORGANISM: Artificial Sequence
<220> FEATURE:
<223> OTHER INFORMATION: Primer-R2
<220> FEATURE:
<221> NAME/KEY: misc_feature
<223> OTHER INFORMATION: Synthetic

<400> SEQUENCE: 5
ttcgccccat tggctcct    18

<210> SEQ ID NO 6
<211> LENGTH: 27
<212> TYPE: DNA
<213> ORGANISM: Artificial Sequence
<220> FEATURE:
<223> OTHER INFORMATION: Probe 2
<220> FEATURE:
<221> NAME/KEY: misc_feature
<223> OTHER INFORMATION: Synthetic

<400> SEQUENCE: 6
ccggaaaaat ttttgaggaa ccgcagg    27

<210> SEQ ID NO 7
<211> LENGTH: 26
<212> TYPE: DNA
<213> ORGANISM: Artificial Sequence
<220> FEATURE:
<223> OTHER INFORMATION: dual probe general
<220> FEATURE:
<221> NAME/KEY: misc_feature
<223> OTHER INFORMATION: Synthetic
<220> FEATURE:
<221> NAME/KEY: misc_feature
<222> LOCATION: (1)..(12)
<223> OTHER INFORMATION: n is eqaul to a, c. g or t

<400> SEQUENCE: 7
nnnnnnnnnn nnttgaggaa ccgcag    26

<210> SEQ ID NO 8
<211> LENGTH: 55
<212> TYPE: RNA
<213> ORGANISM: Homo sapiens

<400> SEQUENCE: 8
cuauacuagu aaucgccccu caguacggag gaacggggga auccuaggca uggga    55

<210> SEQ ID NO 9
<211> LENGTH: 56
<212> TYPE: RNA
<213> ORGANISM: Homo sapiens

<400> SEQUENCE: 9
cuauacuagu aaucgccccu caguacgaga ggaacgggg aauccuaggc auggga    56